(12) United States Patent
Lowe

(10) Patent No.: US 7,395,133 B2
(45) Date of Patent: Jul. 1, 2008

(54) ENVIRONMENTALLY CONTROLLABLE STORAGE SYSTEM

(76) Inventor: Gregory Earl Lowe, 3848 Coachman Circle, Mississauga, Ontario (CA) L5M 6R4

(*) Notice: Subject to any disclaimer, the term of this patent is extended or adjusted under 35 U.S.C. 154(b) by 79 days.

(21) Appl. No.: 11/205,157

(22) Filed: Aug. 17, 2005

(65) Prior Publication Data

US 2007/0041814 A1 Feb. 22, 2007

(51) Int. Cl.
*B65G 1/00* (2006.01)
*G06F 7/00* (2006.01)

(52) U.S. Cl. .................. 700/218; 700/213; 414/331.02

(58) Field of Classification Search ............ 414/331.02, 414/331.05, 331.06, 283, 223.01, 223.02; 700/218, 213, 214
See application file for complete search history.

(56) References Cited

U.S. PATENT DOCUMENTS

| | | | |
|---|---|---|---|
| 5,271,702 A * | 12/1993 | Dobbs et al. ........... | 414/223.01 |
| 5,546,315 A | 8/1996 | Kleinschnitz | |
| 5,733,024 A | 3/1998 | Slocum et al. | |
| 5,735,587 A * | 4/1998 | Malin et al. .................. | 312/305 |
| 5,893,795 A * | 4/1999 | Perlov et al. ................ | 451/288 |
| 6,129,428 A * | 10/2000 | Helwig et al. ............... | 312/114 |
| 6,357,984 B1 | 3/2002 | Zinger et al. | |
| 6,536,859 B1 * | 3/2003 | Bathe ......................... | 312/305 |
| 2003/0031542 A1 * | 2/2003 | Hamel et al. ........... | 414/331.05 |
| 2003/0091413 A1 * | 5/2003 | Yergenson ............. | 414/331.02 |
| 2004/0175258 A1 | 9/2004 | Haas | |
| 2004/0213651 A1 * | 10/2004 | Malin ..................... | 414/331.05 |

OTHER PUBLICATIONS

CO2 Incubator with Plate Carousel [online] Brandel Corporation, United States [retrieved on Dec. 21, 2005 ], Retrieved from the internet: <URL: http://www.brandel.com/platestorageincubator.html>.
CRS Dimension4™ Modular Automation Platform Product Brochures, Thermo Electron Corporation, United States [published on or before Aug. 17, 2005].
CRS Product Web Pages [online] Thermo Electron Corporation, United States [retrieved on Jan. 26, 2005], Retrieved from the internet: <URL: http://www.thermo.com/com/cda/product/detail/>.
Cytomat 6000 Series Product Web Pages [online] Thermo Electron Corporation, United States [retrieved on Jul. 15, 2005], Retrieved from the internet: <URL: http://www.cytomat.com/products/>.

(Continued)

*Primary Examiner*—Gene O. Crawford
*Assistant Examiner*—Ramya G. Prakasam
(74) *Attorney, Agent, or Firm*—Kevin E. Holbeche; Patrick J. Hofbauer

(57) ABSTRACT

A storage system having one or more storage modules each comprising a substantially cylindrical housing having a curved sidewall portion extending between a top wall portion and a bottom wall portion, with the housing being disposed about a central axis. A carousel is mounted within the housing for controlled rotation about the central axis. The carousel has a plurality of storage locations disposed in vertical arrays about the axis to receive articles to be stored. A first door opening is formed in the sidewall portion to provide for access from the exterior of the housing to at least one of the vertical arrays adjacent to the first door opening. A means for controlling the temperature within the housing is also provided.

21 Claims, 13 Drawing Sheets

OTHER PUBLICATIONS

Meta-Stor: Microplate Bulk Storage [online] Torntec Inc., United States [retrieved on Dec. 21, 2005]Retrieved from the internet: <URL: http://www.torntec.com/pages/products/Mega-Star.html>.

Stelzer et al., Building a Lab System in the 3rd dimension—The Z Axis, Thermo Electron Corporation, Canada [Published on or before Aug. 17, 2005].

* cited by examiner

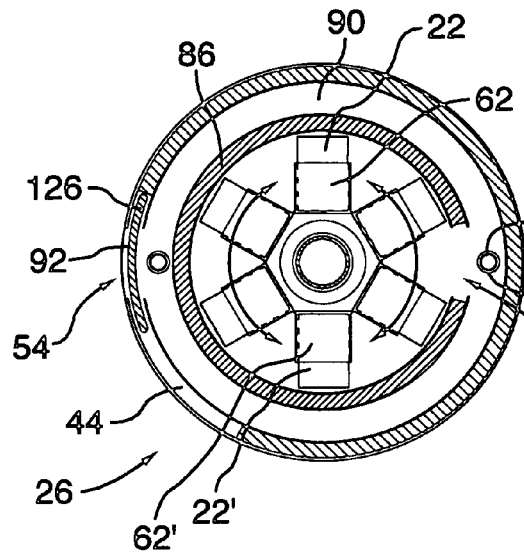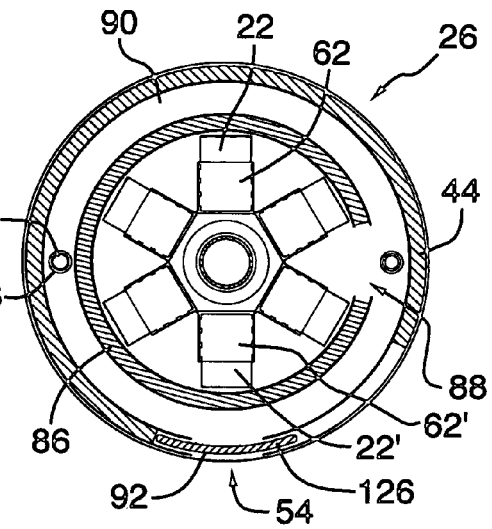
FIG.7A    FIG.7B
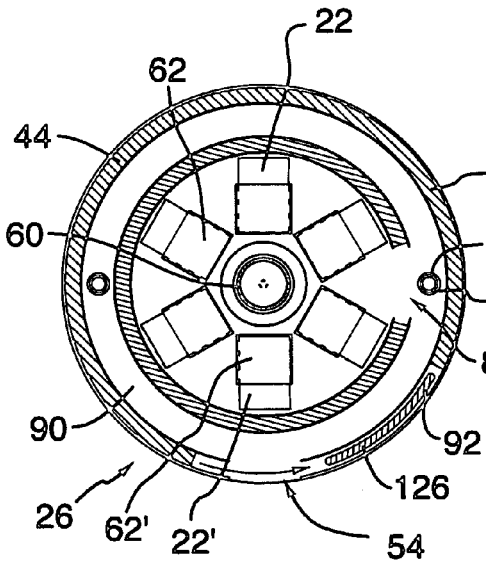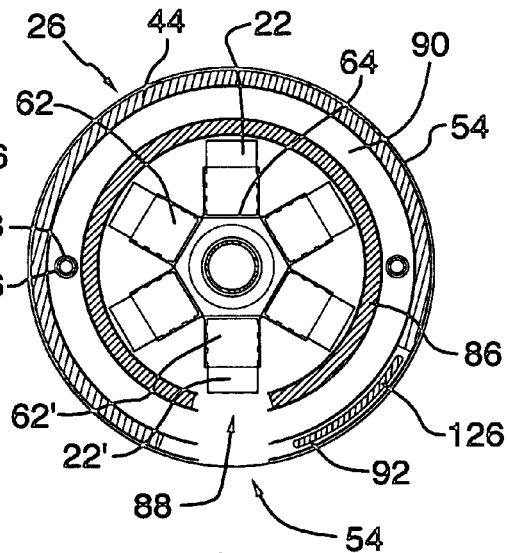
FIG.7C    FIG.7D

ENVIRONMENTALLY CONTROLLABLE STORAGE SYSTEM

FIELD OF THE INVENTION

The present invention relates to storage systems for articles such as microplates, and more particularly to a storage system comprising one or more storage modules each having a controlled internal environment from which said articles may be removed and returned robotically.

BACKGROUND OF THE INVENTION

Medical, chemical and biological laboratories utilize large volumes of microplates and related labware in their drug development and analytical programs, whether for the analysis of chemical or biological samples. To be cost effective, for tracking accuracy, and for reasons of health and safety, most modern high throughput laboratory analysis systems are automated, with extensive use being made of conveyors, robots, and other microplate handling devices integrated into the system to provide for rapid mechanical movement of the microplates in seriatim through a sequence of workstations, such workstations including, without limitation, plate delidders, plate readers, plate flippers, plate shakers, thermocylers and protein crystallography workstations. At each workstation, a pre-determined operation is performed on the respective sample contained in each microplate. Increasingly, such automated systems are under the centralized control of a personal computer ("PC") or other CPU means programmed with commercially available control system software designed for this purpose. Each microplate is typically barcoded or otherwise machine readably marked to allow for the individual identification and tracking of samples throughout the system. Some prior art control system software programs allows for customized processing of identified sub-sets of microplates of a larger run of microplates at one or more of the workstations. Moreover, some of these programs also allows for the accumulation, storage and analysis of statistical data pertaining to the processed samples.

Progressively, such prior art laboratory analysis systems have also become more modular in nature, thus allowing for the number, type and sequence of workstations to be re-organized and re-configured without the need for extensive re-design of the system hardware or software from scratch. This modularization has been facilitated by several factors, including, without limitation, the standardization of microplates and related labware to published industry standards, the increasing availability of standardized processing hardware (e.g. plate movers and workstations) having standardized electrical interfaces for easy connection to PC's, and the availability of increasingly versatile and user friendly control system software to run on such PC's.

More recently, in order to conserve valuable laboratory floor space, such high volume automated laboratory analysis systems have moved from strictly linear layouts, such as utilized in, for example, the CRS Model HSDM 40 MBS system available from Thermo Electron Corporation, of Burlington, Ontario, Canada, wherein a series of 40 thermocylers is laid out 20 on each side of a linear microplate transport axis defined by a conveyor belt based plate mover, to systems having a more dense three-dimensional layout, such as utilized, for example, in the CRS Model VAL 40 MBS system also available from Thermo Electron Corporation, of Burlington, Ontario, Canada, wherein 40 thermocylers are arranged in a semi-circular outline of 8 vertical banks, each bank having 5 thermocycler units stacked one above the other, with the 8 banks surrounding a robot having a SCARA arm which is able to grip a microplate and rapidly and accurately move it from a defined pick-up location to any one of the 40 thermocycler units and to subsequently retrieve the microplate from that thermocycler unit for return to its original location, or to another location within its reach, for subsequent processing by the automated analysis system.

Such advances in the prior art have not only reduced the space requirements for high throughput automated laboratory analysis systems, but have also significantly reduced the lost motion and long transport times associated with prior art systems laid out on a two-dimensional linear geometry. As such, the processing bottleneck in high throughput automated laboratory screening and analysis systems utilizing microplates has shifted from delivery and retrieval of the microplates to and from the workstations of the system to delivery of the microplates from storage into the automated system. This is so as known automated processing systems, such as those discussed above, typically have a storage facility of limited capacity connected directly to the system from which it can draw microplates for automated processing. An on-line storage facility of this type typically comprises a carousel having from six to eight removable "nests" (or "hotels") each accommodating the storage of from about 20 to about 30 microplates. These nests are typically releasably hung around the outer circumference of the carousel frame for automated feeding into the laboratory analysis system by robots or other plate moving means. An example of such a carousel, with fixed nests, can be seen in U.S. patent applications Ser. No. 10/735,866 (Hass) published under Publication No. US 2004/0175258 on Sep. 9, 2004. An example of such a carousel, with removable nests, is the CRS Microplate Carousel available from Thermo Electron Corporation, of Burlington, Ontario, Canada. Not only are such prior art carousel storage devices unduly heavy and complex, due in part to the separate mounting hardware typically used to provide for such releasable mounting of the nests, but they must additionally provide plate locators on the nests to positively locate the microplates relative to the nests for accurate robotic gripping. Additionally, and more importantly, such on-line storage facilities must be continually replenished from a larger, standalone storage facility that is off-line (e.g. a larger refrigerated housing or heated incubator) typically containing many hundreds, if not thousands of microplates. This task is, in the prior art, typically carried out manually by laboratory personnel who restock the empty nests of the on-line storage facility with microplates retrieved from the off-line storage facility. Such work is not only tedious and time consuming, but keeps laboratory personnel from doing higher level tasks. Moreover, failure to timely replenish the on-line storage facility from the off-line storage facility may result in costly shutdowns of the automated system due to lack of microplates for processing.

It should also be considered that microplates manually loaded into the on-line storage facility for subsequent processing by the automated system are more likely to be subject to sequencing errors (i.e., being mixed up in their order) than machine identified and loaded microplates. Such sequencing errors can result in the samples contained within the microplates being improperly processed at the workstations of the system, as the position of each respective microplate within the system is based on the assumption that laboratory personnel initially set-up the on-line storage facility according to the worklist provided. Thus, such sequencing errors of the microplates can have potentially dire consequences. Additionally, manual movement of the microplates from the off-line storage facility and loading thereof into the on-line storage facility is subject to mishap (e.g., dropping of the microplates), with resultant loss of the samples contained within the microplates.

The above problems with prior art microplate storage facilities are compounded where the storage must be environmentally controlled, i.e., maintained at a temperature that is not ambient to the processing system. For example, it is known to store microplates for subsequent automated processing at temperatures that vary between about 95° Celsius to about minus 80° Celsius with varying controlled levels of humidity and $CO_2$. In such cases, prior art environmentally controlled storage devices are severely limited for several additional reasons. With respect to environmentally controlled on-line microplate storage facilities, a well-known line of such devices is the Cytomat 6000 Series of automated incubators, available from Thermo Electron Corporation of Burlington, Ontario, Canada, which devices have a conventional storage carousel centrally positioned inside of a bulky, cuboidal incubated housing enclosure. Such large and bulky cuboidal housing enclosures prevent the nesting of these types of devices in sufficiently close proximity to one another to allow for efficient multiple placement around a centralized external microplate mover or robot, particularly where a circular or semi-circular array of the subject devices is desired to minimize the floorprint of the system. Moreover, the housing enclosure of such prior art environmentally controlled microplate storage devices have a single robotic arm positioned within the incubated housing enclosure, which robotic arm is limited in its operation to accessing only microplates stored in the carousel nest positioned immediately adjacent to the arm for delivery of such microplates to an area located immediately outside of a small door positioned in a front wall of the housing enclosure. These structural arrangements significantly limit the available options for efficiently incorporating prior art types of environmentally controlled on-line laboratory storage facilities into high throughput automated microplate analysis systems. Further, the placement of the robotic arm and its related equipment inside of an environmentally controlled housing enclosure introduces an extra heat load thereon and causes the robotic arm to operate in conditions of heat, cold, or humidity that may not be optimal to its performance, reliability or longevity. Moreover, such an extra heat load may cause temperature variations in the microplates positioned in proximity to the robotics. Such local temperature variations can cause undesirable effects on the sample characteristics, thus producing an uncontrolled basis of experimentation.

With respect to larger scale environmentally controlled off-line storage facilities, such as walk-up or walk-in refrigerators or incubators, the capacity of these units has to be planned for well in advance of their date of first use, and may often require facility restructuring, particularly in relation to any upsizing subsequent to initial facility construction. Moreover, the capital costs associated with such off-line bulk microplate storage facilities are significant, further limiting their availability.

Thus, there remains a need in the prior art for an improved environmentally controllable storage system suitable for use with microplates. This need is acute in relation to environmentally controllable storage systems for microplates that: (i) are suitable for on-line integration with other automated laboratory analysis equipment; (ii) are scalable to the desired throughput requirements of a user on an ongoing basis over time; (iii) eliminate or substantially reduce the need for large, off-line storage facilities; and (iv) provides for automated testing and analysis purposes an interim, or remote, large scale, mobile, on-line storage capability which obviates the need for restocking of frequently used test samples contained in microplates.

It is thus an object of the present invention to obviate or mitigate at least one of the above mentioned disadvantages associated with prior art storage devices.

SUMMARY OF THE INVENTION

In accordance with one aspect of the present invention there is provided a storage system having one or more storage modules. Each storage module comprises a cylindrical housing having a sidewall portion. The sidewall portion has an external sidewall surface. The external sidewall surface defines a cross-sectional profile of constant positive curvature about an entirety of the exterior of the housing. (In this context, and as used throughout the specification and claims, we adopt the convention that a "positive curvature" exists where a line normal to a chosen surface of a plane curve turns in the same direction as the plane curve; otherwise, the chosen surface of the plane curve is said to have a "non-positive curvature"). The sidewall portion extends between a top wall portion and a bottom wall portion. The housing is disposed about a central axis. A storage carousel is mounted within the housing for rotation about the central axis and has a plurality of storage locations disposed in vertical arrays about the central axis to receive articles, preferably microplates or similar labware. A first door opening is formed in the sidewall portion. The constant positive curvature of the sidewall portion is such as to enable such door opening to be predisposed to provide for access at least from any single location on the exterior of the housing to at least one of the vertical arrays adjacent to the first door opening. A door member is preferably mounted on the housing so as to be movable between an open and a closed configuration so as to selectively occlude the first door opening. An environmental control means for controlling the temperature within the housing is also provided. The first door opening preferably extends axially between the top and the bottom wall portions of the housing, and the door member preferably has a curvature complimentary to the curvature of the sidewall portion, which allows the first door member to move between its aforesaid open and closed configurations by sliding in circumferential nesting relation relative to the sidewall portion of the storage module.

According to another aspect of the present invention, the environmental control means comprises an air flow delivery means positioned within the housing.

According to yet another embodiment of the present invention, there is provided a storage system having one or more storage modules. Each storage module comprises a substantially cylindrical housing having a curved sidewall portion extending between a top wall portion and a bottom wall portion. The housing is disposed about a central axis. A storage carousel is mounted within the housing for rotation about the central axis and has a plurality of storage locations disposed in vertical arrays about the central axis to receive articles, preferably microplates or similar labware. A first door opening is formed in the sidewall portion to provide for access from the exterior of the housing to at least one of the vertical arrays adjacent to the first door opening. An environmental control means for controlling the temperature within the housing is also provided. The housing is mounted atop a base member that preferably has wheels, and the environmental control means comprises a compressor means and a fan means mounted within the base member, preferably so as to remove any heat loading from these components from the housing.

According to still another aspect of the present invention, rotation of the carousel within the housing is driven by a first electrical motor mounted on the module for selective radial alignment of at least one of the vertical arrays with the first door opening. The first electrical motor is preferably drivingly connected to the carousel by a first magnetic coupling means acting on the carousel for this purpose through one or both of the top and bottom wall portions of the housing.

According to still yet a further embodiment of the present invention, the sidewall portion is also mounted so as to be rotatable about the central axis to align the first door opening with a selected one of the vertical arrays. According to this aspect, such rotation of the sidewall portion is driven by a second electrical motor mounted on the module, and this second electrical motor is drivingly connected to the sidewall portion by a second magnetic coupling means acting on the sidewall for this purpose through one, or both, of the top and bottom wall portions of the housing.

According to an additional aspect of the present invention, the aforesaid movement of the door member is driven by a third electrical motor mounted on the module, which electrical motor is drivingly connected to the door member to effect such movement by a third magnetic coupling means acting on the door member through one or both of the top and bottom wall portions of the housing.

According to another aspect of the present invention, a substantially cylindrical baffle wall disposed about the central axis and extending between the top and bottom wall portions is mounted within the housing between the sidewall portion and the carousel to form a vestibule between the sidewall portion and the baffle wall. This baffle wall has a second door opening formed therein. The second door opening preferably axially extends between the top and bottom wall portions of the housing. Moreover, the baffle wall is preferably mounted so as to be rotatable about the central axis, so as to selectively align and misalign the second door opening with the first door opening. Rotation of the baffle wall is preferably driven by a fourth electrical motor mounted on the module, which electrical motor is drivingly connected to the baffle wall to effect such movement by a fourth magnetic coupling means acting on the baffle wall through one or both of the top and bottom wall portions of the housing.

According to yet another aspect of the present invention, an air flow delivery means is positioned in both the vestibule and in the space inside the baffle wall.

According to a further aspect of the present invention, a storage system constructed according thereto further comprises one or more robotic means positioned exterior to the housing and adjacent to the base member of a selected one of said one or more storage modules. Such robotic means are each constructed and otherwise adapted to reach into the housing of said selected storage module through said first door opening, when said door member is in said open configuration, and through said second door opening, when the second door opening is aligned with the first door opening (whether by movement of the sidewall, by movement of the baffle wall, or by coordinated movement of both), thereby to gain access the storage locations disposed in said at least one of the vertical arrays of the carousel, so as to grip and transfer the microplates between said storage locations and the one or more locations exterior to the housing of the selected storage module.

According to a further aspect of the present invention, the storage system comprises a plurality of storage modules positioned in proximity to one another to form a cluster of storage modules, with one or more of the robotic means each positioned within operatively close proximity to at least two of the storage modules of said cluster. With this arrangement, it will be appreciated that the one or more of said robotic means, in combination with one another, provide for the robotic transfer of said articles from the storage locations of any one of the storage modules of the cluster to the storage locations of any other one of the storage modules of the cluster.

According to yet another aspect of the present invention, the first, second, third and fourth electrical motors of each of said storage modules of the cluster and each of said one or more robotic means are in electronic communication with a CPU means programmed with control system software so as to bring each of said robotic means and each of said storage modules under the coordinated control of said CPU means so to form a modular on-line storage system of indefinite capacity, thereby substantially eliminating the need for a standalone off-line mass storage facility.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described hereinbelow.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a exemplary embodiments of the invention will now be illustrated by way of example. It is expressly understood, however, that the drawings are for the purpose of illustration and description only, and are not intended as a definition of the limits of the invention. In the accompanying drawings:

FIGS. 7A through 7D are a sequence of sectional views, similar to FIG. 3B, showing operative movement of the carousel, the curved sidewall portion, the baffle wall and the door member of the storage module to facilitate access from the exterior of the housing to a particular vertical array of storage locations within the housing;

DETAILED DESCRIPTION OF THE INVENTION

Figure 1:
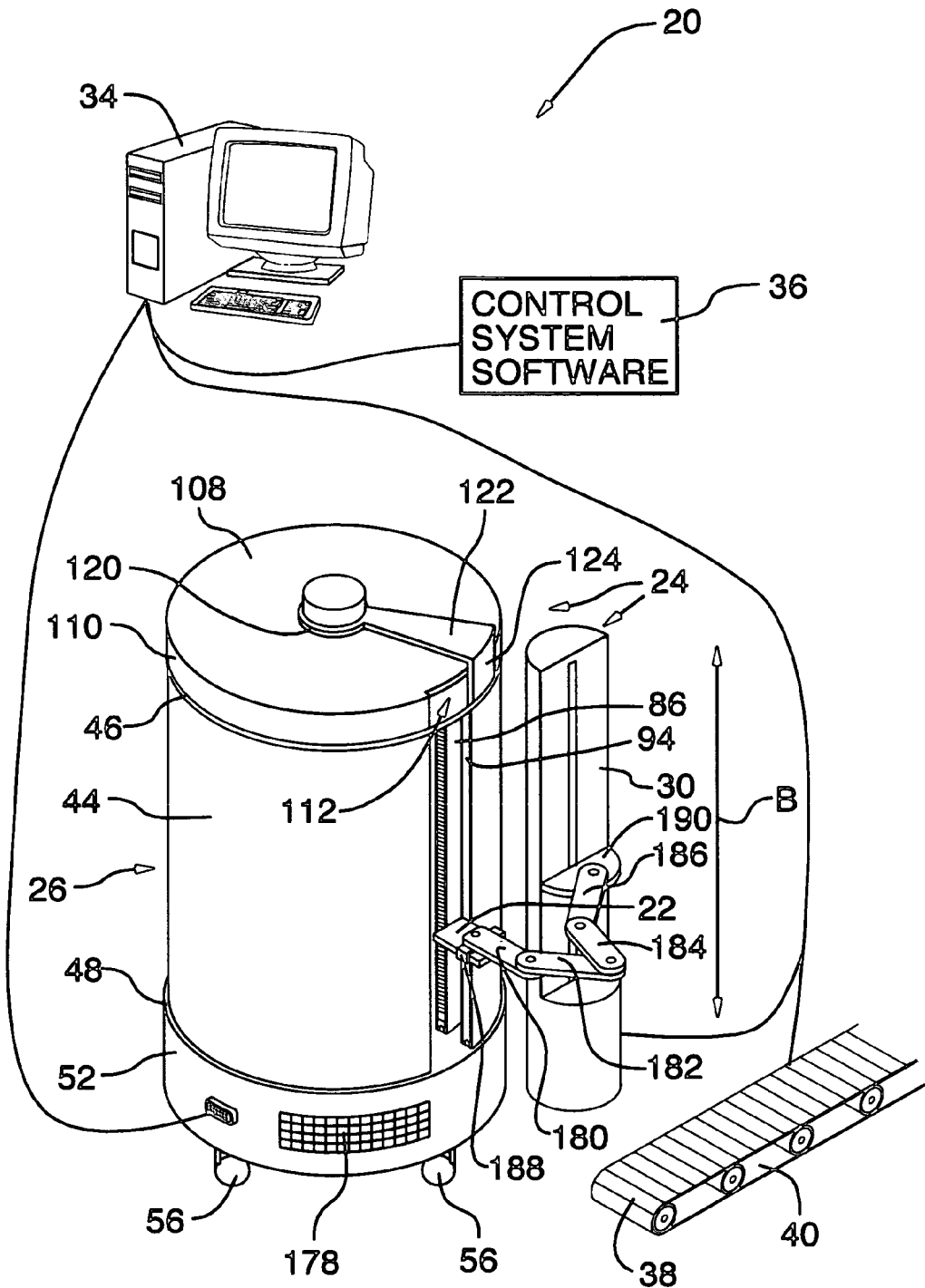
FIG. 1 is a schematic representation of an automated laboratory analysis system incorporating a storage system having a single storage module constructed according to the present invention, with the door member in an open configuration.

Referring to FIG. 1 of the drawings, there will be seen an automated laboratory analysis system 20 which is set up to conduct repetitive tests upon chemical or biological samples (not shown) contained in containers 22 stored in predetermined storage locations 28 (best seen in, for example FIGS. 3A through 3D) in a storage system 24 according to the invention. The containers are typically microplates 22 (that may take a number of known standardized configurations, including, without limitation, deep well microplates). Other types of labware of the same general configuration to the microplates 22 shown may be handled and stored in a manner analogous to that described hereinbelow with routine re-sizing of the necessary components of the invention, as will be readily apparent to those skilled in the art.

The storage system 24 illustrated in the embodiment of FIGS. 1 through 7D comprises a single storage module 26 and a single robotic means 30. This is for ease of illustration, only. That is, it is fully envisioned and intended by the inventor that the present invention expressly relates to and covers more extensive storage systems having a plurality of storage modules 26 arranged into clusters of such modules, and a corresponding plurality of associated robotic handling means. Two examples of such more extensive storage systems are disclosed in FIGS. 8A through 8F, and FIG. 9, respectively. It will be further appreciated by those skilled in the art that the groupings of storage modules and robotic means shown in these latter two embodiments are themselves modular in nature, and can be extended indefinitely in at least two dimensions so as to provide a corresponding indefinite quantity of storage capacity for microplates 22, limited only by the floor space of the subject storage facility. Like reference numerals will be used in all of the figures herein to designate analogous structures, irrespective of the embodiment in which they appear.

The storage module 26 and robotic means 30 of FIG. 1 are both in electronic communication with a CPU means conventionally mounted within a personal computer ("PC") 34. The PC 34 is programmed with control system software 36 (such as, for example, the POLARA™ control system software available from Thermo Electron Corporation of Burlington, Ontario, Canada), which software 36 causes the various components of the storage system 24 to move in a coordinated and controlled manner (as described more fully herein) so as to allow the robotic means 30 to robotically grip a selected microplate 22 in its predetermined storage location 28 within the storage module 26 and thereafter transfer the microplate 22 to one or more locations exterior of the storage module 26. Such a location may include, for example, a workstation (not shown), or the head area 38 of a conventional microplate conveyor 40, which microplate conveyor transports microplates 22 placed thereon to the vicinity of a remote workstation (not shown) of the laboratory analysis system 20 removed from the vicinity of the storage system 24, for further automated operations of the laboratory analysis system 20 to be carried out thereon. Of course, the robotic means 30 may also be programmed, as required, to grip and pick up the microplate 22 from the head area 38 of the plate conveyor 40 for return to its original predetermined storage location 28.

The storage module 26 shown in each of the three embodiments described herein is substantially identical in all material respects. Having particular regard to FIGS. 1 through 7D, it will be seen that the storage module 26 comprises a housing 42 having a curved sidewall portion 44 which extends vertically between a top wall portion 46 and a bottom wall portion 48 of the housing 42. The housing 42 thus comprised is substantially cylindrical, and is disposed about a vertically oriented central axis "A", (best seen in FIG. 3A). The housing 42 is preferably mounted atop a cylindrical base member 52, with the top wall of the base member 52 being the bottom wall 48 of the housing 42. The base member 52 is preferably provided with a plurality of conventional wheels or swivel castors 56 which depend downwardly from its bottom surface 58 to facilitate selective movement of the storage module 26 from place to place on the floor of the laboratory facility (not shown). The wheels or swivel castors 56 preferably number three or four, and are of the known type that may be locked against rotation, once the storage module 26 is desirably positioned.

Figure 3A:
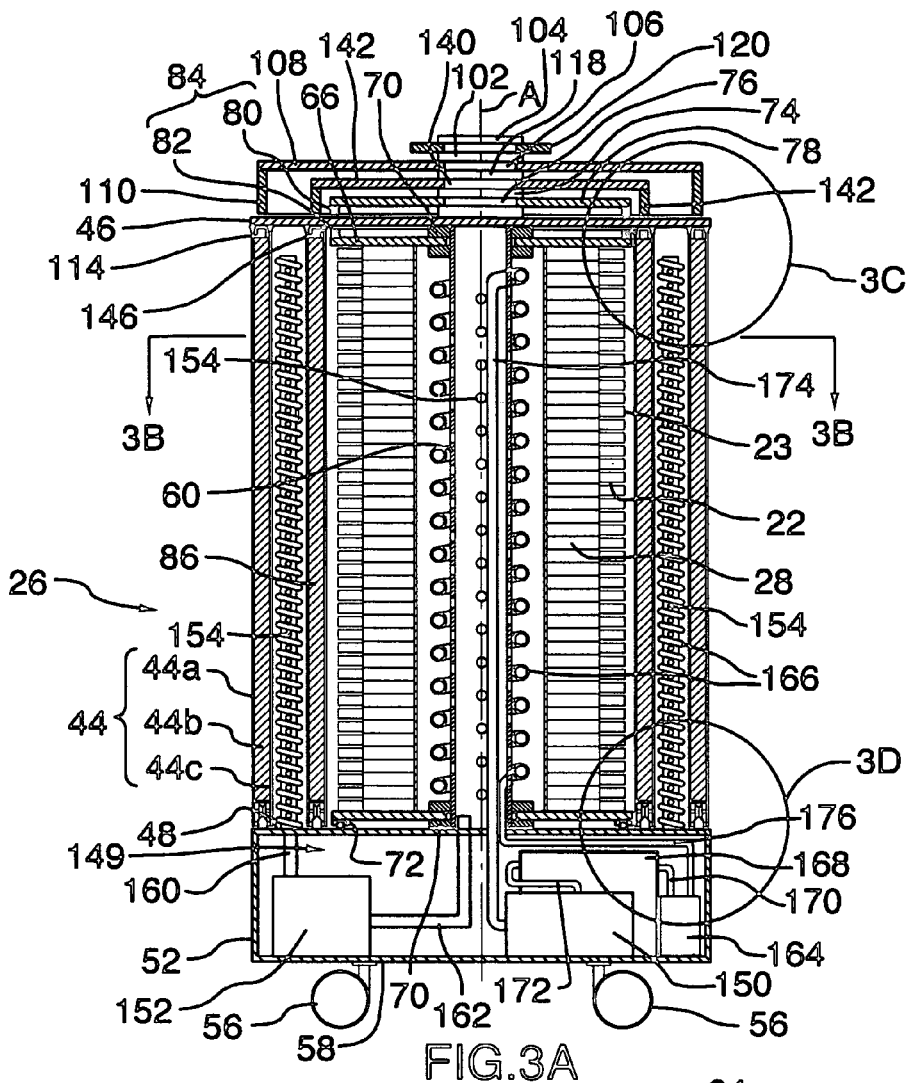
FIG. 3A is sectional view along sight line 3A-3A of FIG. 2.
Figure 3B:
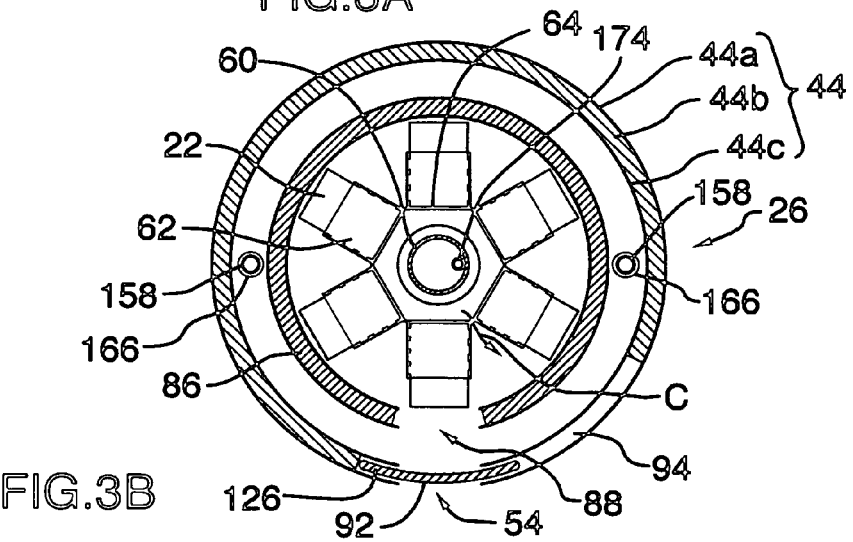
FIG. 3B is a sectional view along sight line 3B-3B of FIG. 3A.

The curved sidewall portion 44 of the housing 42 is preferably thermally insulated, having three distinct layers as follows: an outer skin (hereinthroughout, alternately referred to as an "external sidewall surface") 44a of lightweight metal or plastics material; a middle layer 44b of polyurethane foam, or other insulating material; and, an inner skin 44c of the same, or similar, material as the outer skin 44a. As best seen in FIG. 3B, the external sidewall surface 44a defines a cross-sectional profile of constant positive curvature about an entirety of the exterior of the housing 42. A first door opening 54 is formed in the curved sidewall portion 44 by a discontinuity of the curved sidewall portion 44, and preferably axially extends the full height of the housing 42 between the top wall portion 46 and the bottom wall portion 48. Of course, the circumferential extent of the first door opening is larger than the width of a microplate 22, and is sized to readily permit the robotic means 30 to gain access through the first door opening 54 into the interior of the housing 42 for inserting and removing microplates 22 from the interior of the housing 42. Moreover, the constant positive curvature of the sidewall portion 44 is such as to advantageously enable the first door opening 54 to be predisposed to provide for such access, by the robotic means 30, at least from any single location on the exterior of the housing 42.

Figure 2:
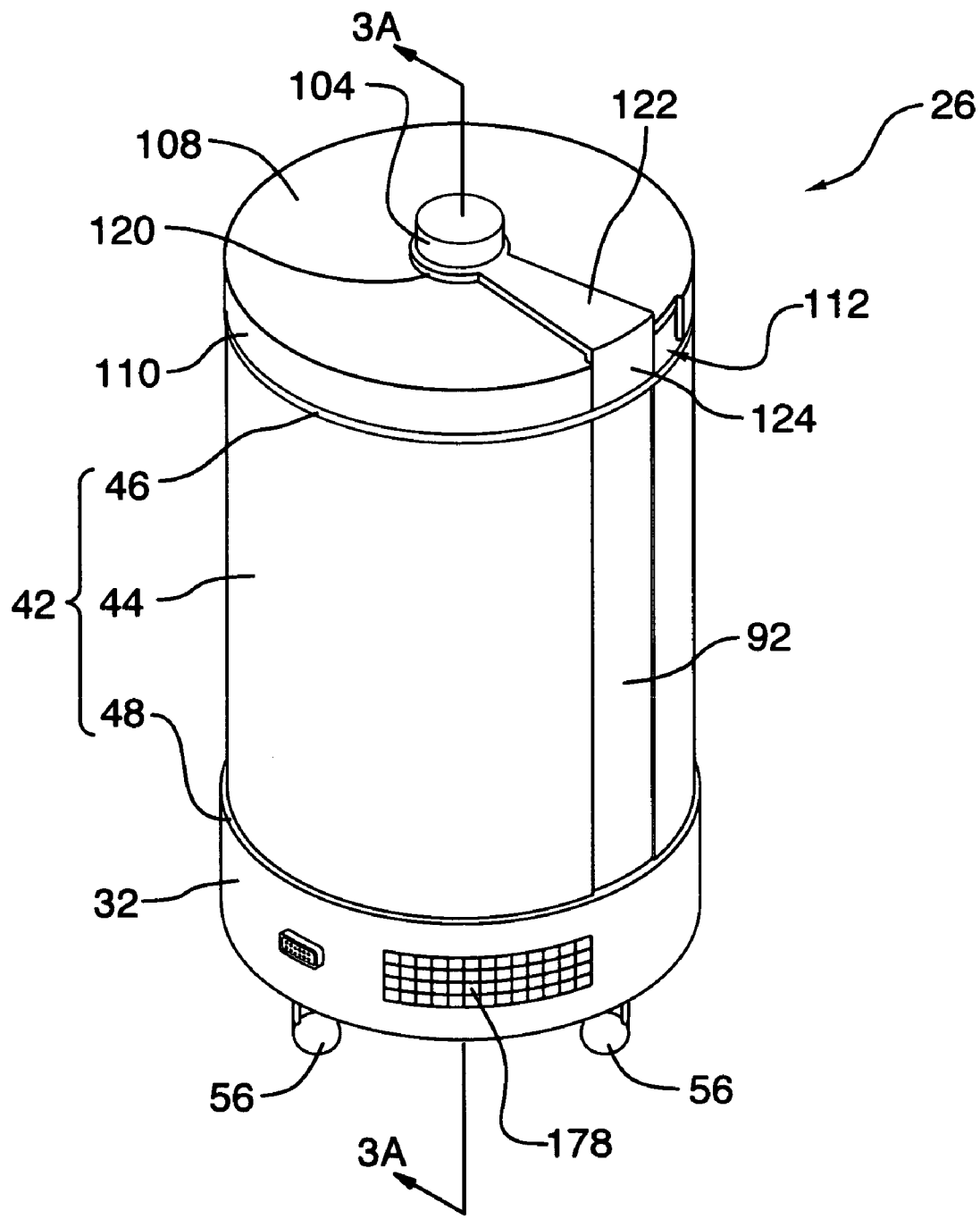
FIG. 2 is a perspective view of the storage module of FIG. 1, with its door member in a closed configuration.
Figure 3C:
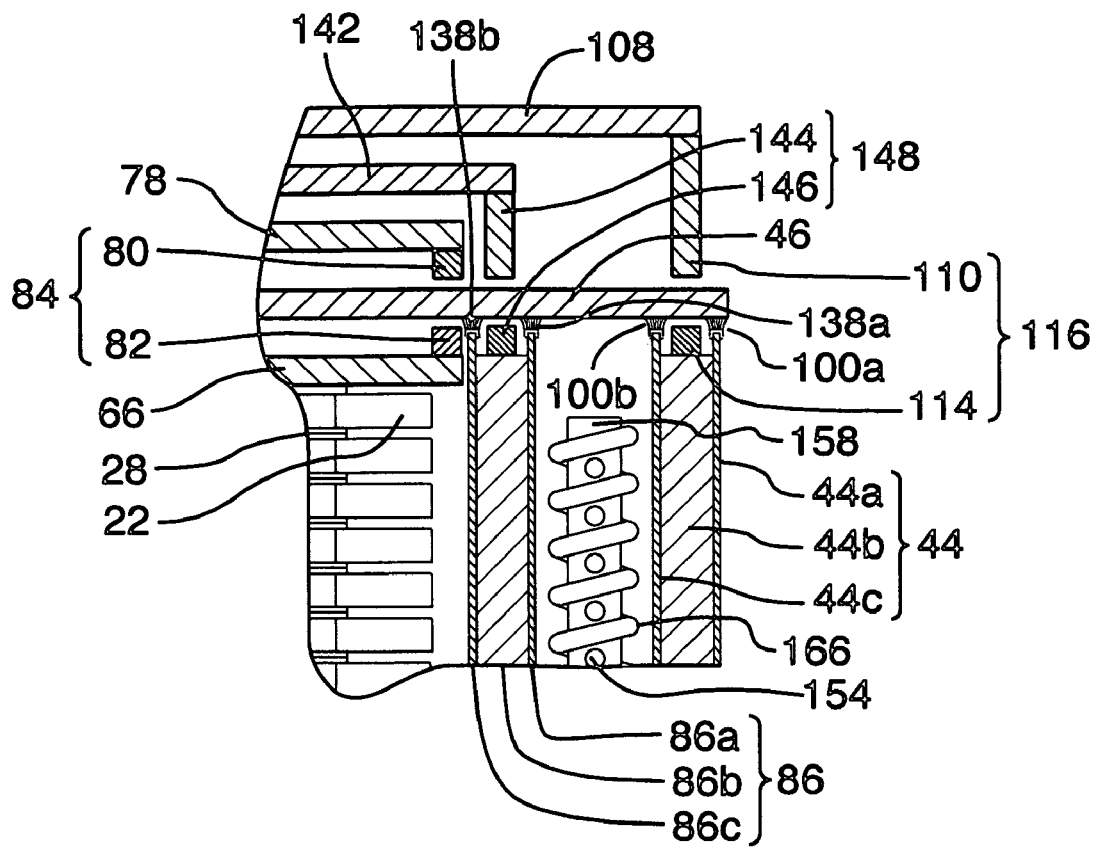
FIG. 3C is a partial view, on an enlarged scale, of the encircled area 3C of FIG. 3A.
Figure 3D:
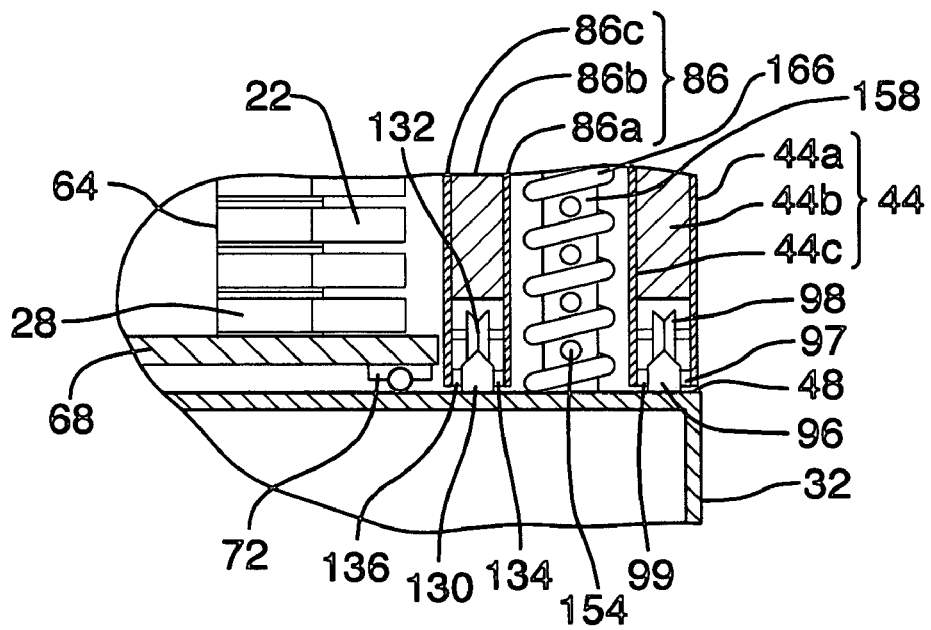
FIG. 3D is a partial view, on an enlarged scale, of the encircled area 3D of FIG. 3A.
Figure 3E:
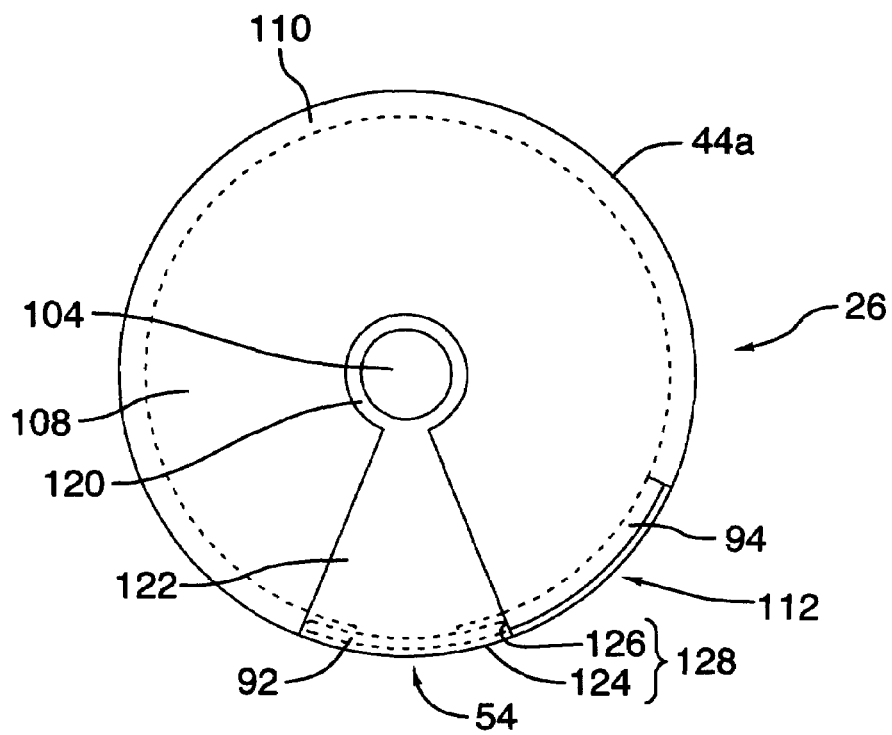
FIG. 3E is a top plan view, partly in phantom outline, of the storage module of FIG. 2, with the door member shown in its closed configuration.
Figure 3F:
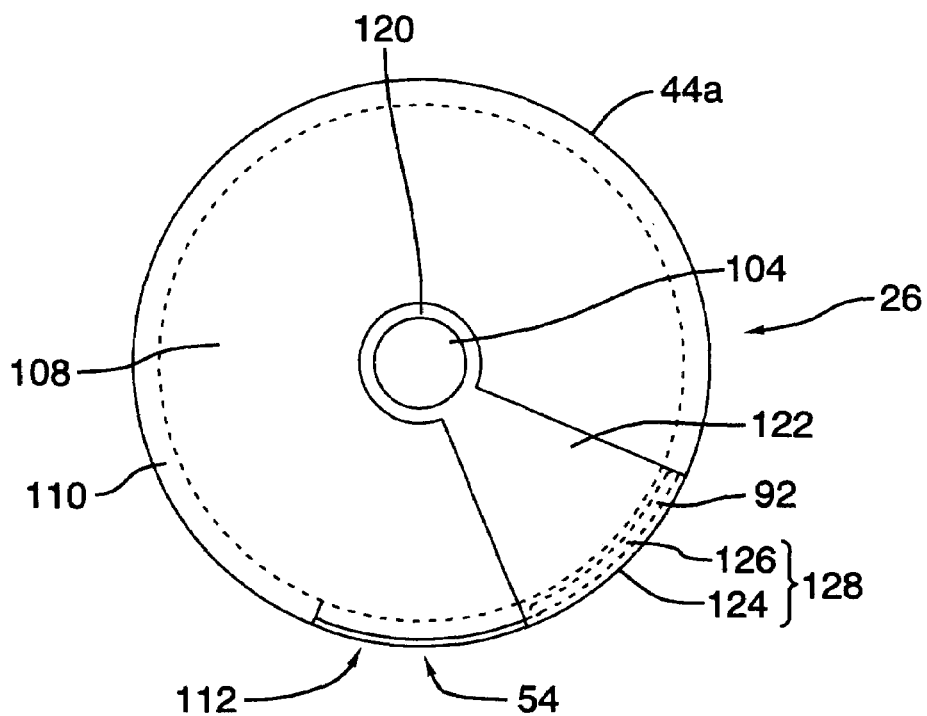
FIG. 3F is a view similar to FIG. 3E, with the door member of the module in its open configuration.
Figure 4:
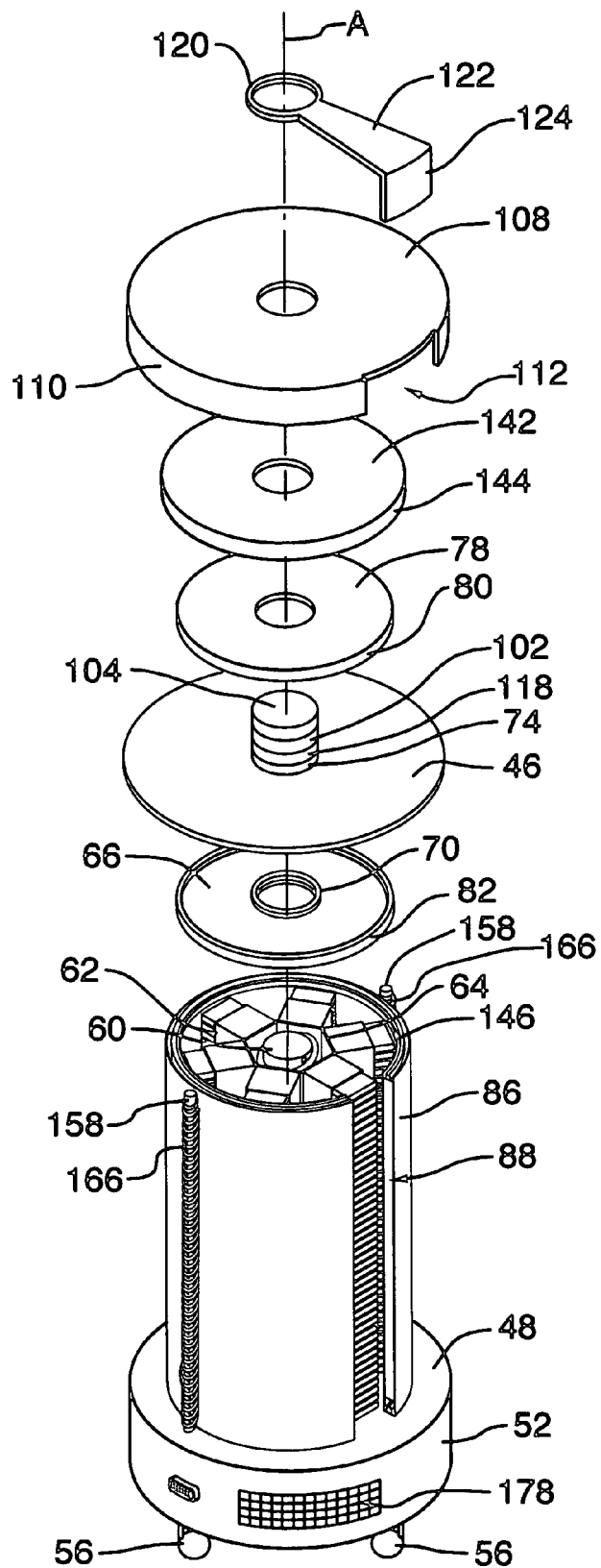
FIG. 4 is a partially exploded view of the storage module of FIG. 2, with the curved sidewall and door member removed to better illustrate components of the module internal to the curved sidewall.
Figure 5:
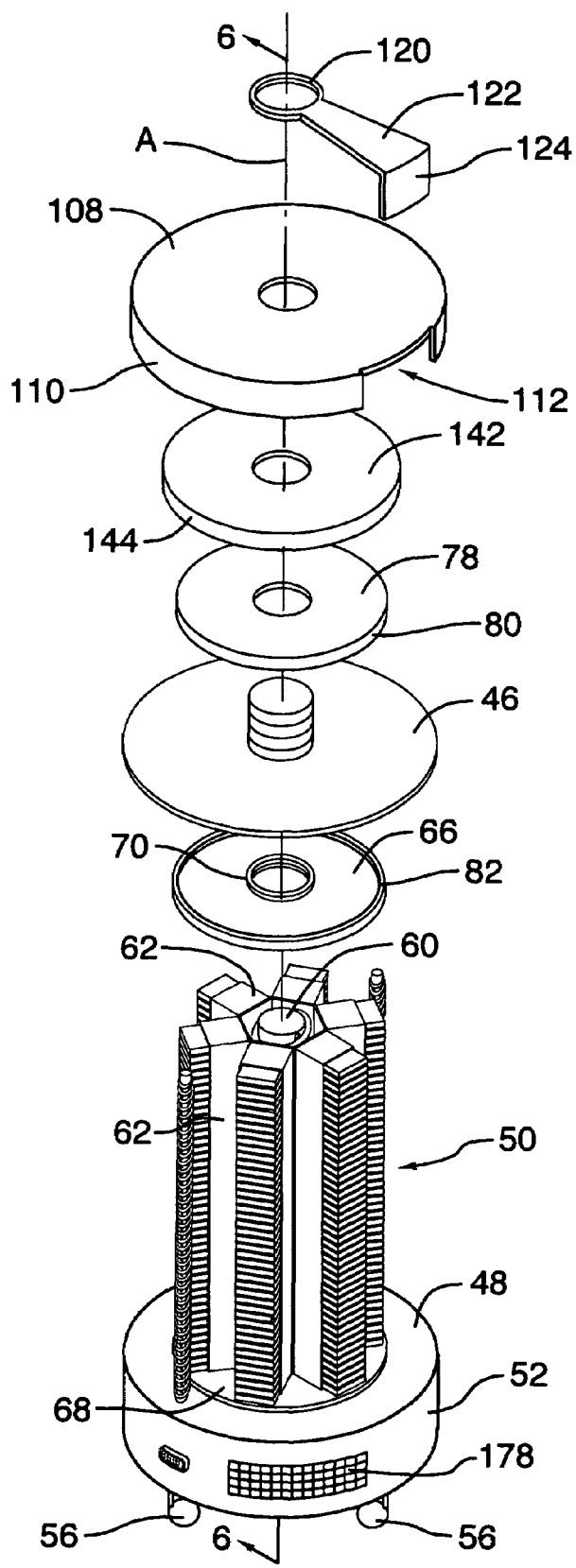
FIG. 5 is a view similar to FIG. 4, with the baffle wall of the module also removed to better illustrate components of the module internal to the baffle wall.

For thermal efficiency, it is preferred to selectively occlude the first door opening 54 by means of a door member 92 that is mounted on the housing 42 and movable between an open configuration (seen in, for example, FIGS. 1 and 3F), and a closed configuration (seen in, for example, FIGS. 2 and 3E). The door member 92 is preferably formed with a complimentary curvature to the curved sidewall portion 42, so as to permit it to move between said open and closed configurations by sliding in circumferential nesting relation relative to the sidewall portion 42 of the module 26. In the embodiments illustrated, the door member 92 is mounted in a cavity 94 formed between the outer skin 44a and the inner skin 44c of the curved sidewall portion 44, from which cavity 94 the material of the middle insulating layer 44c is absent. With this arrangement, the inner 44c and outer 44a skins of the curved sidewall portion act as slide guides for the door member 92 as it moves between said open and closed configurations.

A carousel 50 for storage of the microplates 22 is mounted within the housing 44 for rotation about the central axis "A". The carousel has a plurality of storage locations 28 disposed in six vertical arrays arranged about the vertical axis "A". Each of the vertical arrays constitutes, as illustrated, a fixed nest 62 which has forty-two distinct storage locations 28 positioned one above the other with each capable of accommodating one microplate 22 in fully supported relation. The six fixed nests 62 are joined to one another along their vertical side edges to form a composite nest structure having an inside perimeter wall 64 of hexagonal cross-section (see, for example, FIG. 3B). A circular top plate 66 is attached to the top ends of each of the nests 62 by bolts or other affixation means (not shown). A circular bottom plate 68 is similarly attached to the bottom ends of each of the nests 62. Each of the top 66 and bottom 68 plates have a central aperture fitted with a respective mounting flange 70, each of which mounting flanges 70 is adapted to have fitted therein and carry a bearing collar 72. A central support column 60 is rigidly mounted atop the base member 52 by attachment to the bottom wall 48 in alignment with the central axis "A". The bearing collars 72 are each sized and otherwise adapted to closely fit around the outer circumference of the central support column 60 in rotationally operative sliding relation thereto. A bearing carriage ring 72 is preferably fitted to the underside of the bottom plate 68 of the carousel 50 adjacent to its outer circumferential extent so as to support the carousel 50 above the bottom wall portion 48 of the housing 42 in rotationally rolling relation thereon. In this manner, the carousel 50 is mounted within the housing 42 for rotation about the central axis "A" so as to bring a selected one of said nests 62 into radial register with the first door opening 54, when it is desired to remove or insert a microplate 22 from, or into, a particular storage location 28 positioned within said nest 62.

Figure 6:
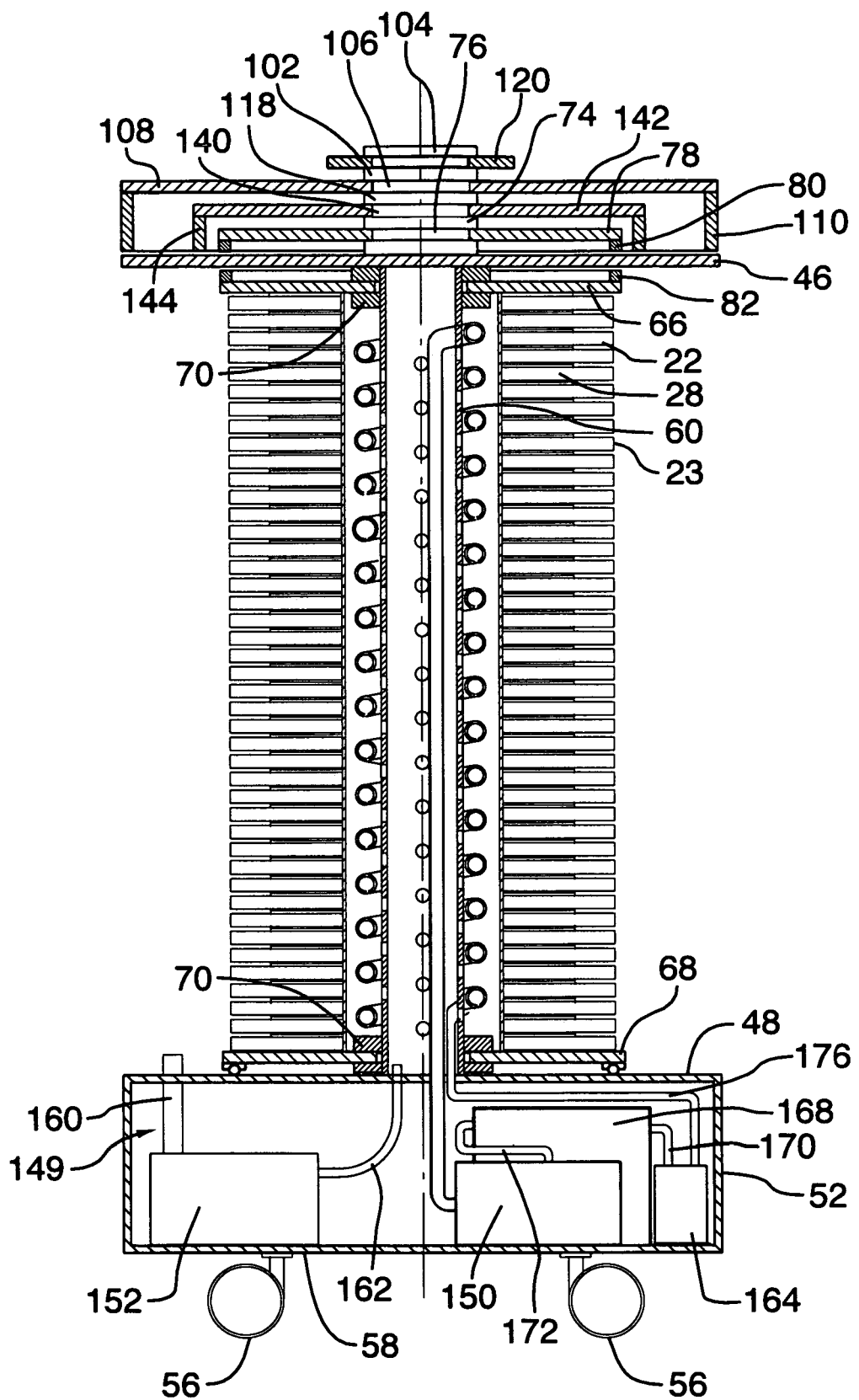
FIG. 6 is sectional view along line sight 6-6 of FIG. 5.

Rotation of the carousel 50 within the housing is under the driving force of a first electrical motor 74 mounted atop the central support column 60. The first electrical motor 74 is circular in plan outline, centered about the axis "A", and has an outer cylindrical first drive collar 76 which engages for rotation therewith a cylindrical first drive plate 78. The first drive plate 78 has arranged about its peripheral edge, in downwardly depending relation therefrom, a first magnetic ring member 80. The first magnetic ring member extends substantially around the circumference of the first drive plate 78, and may be formed as a permanent magnet (as illustrated), or may be formed as an electro-magnet (not illustrated), in which latter case additional circuitry and power supply means to provide for energization of the electromagnet would be additionally required. It is believed that the design and provision of such circuitry and power supply means is within the routine competence of an ordinary person skilled in this art. A second magnetic ring member 82 of opposite polarity to the first magnetic ring member 80 is affixed to the top plate 66 in upwardly projecting relation adjacent its circumferential outer edge for rotation therewith upon rotation of the carousel 50. As best seen in FIGS. 3A and 6, the second magnetic ring member 82 lies beneath the top wall portion 46 of the housing 42 in underlying alignment with the first magnetic ring member 80. Thus, with this arrangement, rotation of the first electrical motor 74 causes rotation of the first drive plate 78 with its attached first magnetic ring member 80. Such rotation of the first drive plate 78, in turn, exerts a moving magnetic force on the second magnetic ring member 82 therebelow, which force drags the second magnetic ring member 82 (together with the attached carousel 50) in the same rotational direction as the first drive plate 78. In this manner, the first magnetic ring member 80 and the second magnetic ring member 82, mounted respectively on the first drive plate 78 and the top plate 66 of the carousel, combine to form a first magnetic coupling means 84 (see FIG. 3C) acting on the carousel 50 through the top wall portion 46 of the housing 42 capable of driving the carousel 50 in either rotational direction under the control of the first electrical motor 74 for selective radial alignment at any particular time (as called for by the programmed computer 34) of at least one of the nests 62 with the first door opening 54.

In order to provide for greater design flexibility by allowing for the placement of a plurality of robotic means 30 at different positions around the periphery of a particular storage module 26, and for allowing access by each of said robotic means 30 from said different positions to the interior of each storage module 26, and in order to lessen the time necessary for any particular robotic means 30 to access a specific microplate 22 contained within a storage location 28, it is desirable that the curved sidewall portion 44 of each such module 26 be rotatable about the central axis "A", so as to bring the first door opening 54 into radial registry with any respective nest 62 containing the specific storage location 28. As best seen in FIGS. 3A and 3D, this may be accomplished by affixing a raised circular track 96 on the bottom wall portion 48 of the housing 42, which track 96 frictionally engages a series of roller wheels 98 arranged around the bottom edge of the curved sidewall 44 in downwardly projecting, substantially evenly spaced relation. An external low friction seal 97 and an internal low friction seal 99 are preferably provided adjacent the lower ends of the outer skin 44a and the inner skin 44c for sliding contact with the sidewalls of the circular track 96 so as to radially locate the curved sidewall portion 44 relative to the track 96 as it rotates and to improve hermetic sealing with the circular track, 96. These low friction seals 97 and 99 may be constructed from nylon, graphite impregnated nylon, or any other low friction material. As best seen in FIGS. 3A and 3C, a pair of circular brush seals is preferably attached to the curved sidewall portion 44 adjacent its the top edge, in frictional contact with the top wall portion 46 of the housing 42, thereby to improve hermetic sealing therewith. The pair of brush seals is comprised of an outer seal 100a attached to the top of the outer skin 44a and an inner seal 100b attached to the top of the inner skin 44c. In this manner, the curved sidewall portion 44 of the housing 42 is able to rotate in either rotational direction about the axis "A" in order to bring the first door opening 54 into aligned radial registry with any selected one of the vertical arrays, being the nests 62, of the carousel 50.

Rotation of the curved sidewall 44, as just described, is under the driving force of a second electrical motor 102 mounted atop a fourth electrical motor 118 (described more fully below), which fourth motor 118 in turn is mounted atop the first electrical motor 74. As previously described, the first electrical motor 74 is mounted atop the central support column 60. Both of the second 102 and fourth 118 electrical motors are of congruent circular plan outline and are each centered about the axis "A". The second electrical motor 102 has an outer cylindrical second drive collar 106 which engages, for rotation therewith, a cylindrical second drive plate 108. The second drive plate 108 has arranged about its peripheral edge, in downwardly depending relation therefrom, a third magnetic ring member 110. The third magnetic ring member 110 extends substantially around the circumference of the second drive plate 108, with the exception of an arc of discontinuity 112 of approximately 20-30 degrees of rotation, which arc 112 defines the range of sliding movement for the door member 92 as it moves between its open to its closed configurations, as described more fully below. The third magnetic ring member 110 may be formed as a permanent magnet (as illustrated), or may be formed as an electromagnet (not illustrated), in which latter case additional circuitry and power supply means to provide for energization of the electromagnet would additionally be required. It is believed that the design and provision of such circuitry and power supply means are within the routine competence of an ordinary person skilled in this art. A fourth magnetic ring member 114 of opposite magnetic polarity to the third magnetic ring member 110 is affixed to the top edge of the curved sidewall portion 42 between the outer 44*a* and inner 44*c* skins of the sidewall portion 42 in upwardly projecting relation adjacent its circumferential outer edge for rotation therewith upon rotation of the curved sidewall portion, as best seen in FIGS. 3A and 3C. The fourth magnetic ring member 114 lies beneath the top wall portion 46 of the housing 42 in underlying alignment with the third magnetic ring member 110. With this arrangement, rotation of the second electrical motor 102 causes rotation of the second drive plate 108 with its attached third magnetic ring member 110. Thus, such rotation of the second drive plate 108, in turn, exerts a moving magnetic force on the fourth magnetic ring member 114 therebelow, which force drags the fourth magnetic ring member 114 (together with the attached sidewall portion 44) in the same rotational direction as the second drive plate 108. In this manner, the third magnetic ring member 110 and the fourth magnetic ring member 114, mounted respectively on the second drive plate 108 and the top edge of the curved sidewall portion 44 of the housing 42, combine to form a second magnetic coupling means 116 (see FIG. 3C) acting on the curved sidewall portion 44 through the top wall portion 46 of the housing 42, which second magnetic coupling means 116 is capable of driving the curved sidewall portion 44 in either rotational direction under the control of the second electrical motor 102 for selective radial alignment at any particular time (as called for by the programmed computer 34, and with the coordinated rotation of the carousel 50) of at least one of the vertical arrays (i.e., nests 62) with the first door opening 54.

The sliding movement of the door member 92 from its open configuration (seen in, for example, FIGS. 1 and 3F) to its closed configuration (seen in, for example, FIGS. 2 and 3E) is driven by a third electrical motor 104 mounted on the central support column 60 atop the first 74, second 102, and fourth 118 electrical motors. The third electrical motor 104 is, like the other electrical motors 74, 102 and 118, of congruent circular plan outline, and is centered about the axis "A". The third electrical motor 104 is drivingly gripped by a drive take-off ring 120, which ring projects radially outwardly to form a sectored drive plate 122. The sectored drive plate 122 has arranged around its peripheral edge, in downwardly depending relation therefrom, a first magnetic sector plate 124. The first magnetic sector plate 146 extends circumferentially through an arc that is continuous with, and substantially one half of the extent of, the arc of discontinuity 112, (i.e., approximately 10-15 degrees of rotation), and is intended to have approximately the same circumferential extent as the door member 92 lying below it. The first magnetic sector plate 124 may be formed as a permanent magnet (as illustrated), or may be formed as an electromagnet (not illustrated), in which latter case additional circuitry and power supply means to provide for energization of the electromagnet would be additionally required. It is believed that the design and provision of such circuitry and power supply means would be within the routine competence of an ordinary person skilled in this art.

A second magnetic sector plate 126 of opposite polarity to the first magnetic sector plate 146 is affixed to the top edge of the door member 92 in upwardly projecting relation, for sliding movement with the door member 92. The second magnetic sector plate 126 (see FIGS. 7A through 7D) lies beneath the top wall portion 46 of the housing 42 in underlying alignment with the first magnetic sector plate 124. Thus, with this arrangement, rotation of the third electrical motor 104 causes coincident rotation of the sectored drive plate 122 and of the first magnetic sector plate 146. Such rotation, in turn, exerts a moving magnetic force on the second magnetic sector plate 126 therebelow, which carries the door member 92 attached thereto in the same rotational direction as the sectored drive plate 122. In this manner, the first magnetic sector plate 124 and the second magnetic sector plate 126, mounted respectively on the sectored drive plate 122, combine to form a third magnetic coupling means 128 acting on the door member 92, through the top wall portion 46 of the housing 42, to drive the door means 92 in either rotational direction (under control of the third electrical motor 104) corresponding to opening and closing of the door member 92, as seen in FIGS. 2E and 3E (closed configuration) and 1 and 3F (open configuration).

There is also, for reasons of thermal efficiency, preferably provided within the cylindrical housing 42 a substantially cylindrical baffle wall 86 extending vertically between the top wall portion 46 and the bottom wall portion 48 of the housing. The baffle wall 86 is mounted, as shown, between the sidewall portion 44 and the carousel 50, thus forming a vestibule 90 between the sidewall portion 44 and the baffle wall 86. The longitudinal axis of the baffle wall 86 is preferably aligned with the central axis "A" of the housing 42. The baffle wall 86 is also preferably of a similar tri-laminar construction as is the sidewall portion 44, having an outer skin 86*a* of lightweight metal or plastics material, a middle layer 86*b* of polyurethane foam, or other insulating material; and an inner skin 86*c* of the same, or similar, material as the outer skin 86*a*. Thus, the baffle wall 86 and vestibule 90 act as an insulating layer interposed between the microplates 22 and the first door opening 54. A second door opening 88 is formed in the baffle wall 86 by a discontinuity of the arc formed by the baffle wall 86, and said second door opening 88 preferably axially extends between the top 46 and the bottom 48 wall portions of the housing 42, in the same general manner as the first door opening 54. Moreover, the second door opening 88 is of substantially the same circumferential extent as the first door opening 54, such then when both door openings 54 and 88 are in radial register with one another, the circumferential edges of each are in substantial radial alignment. When the first 54 and second 88 door openings are aligned in this manner, it is possible to rotate the carousel 50 in the manner described above, so as to bring any selected one of the fixed nests 62 in to alignment with the door openings 54, 88, thereby to facilitate removal/replacement of a microplate 22 assigned to a storage location 28 in said nest 62 by the robotic means 30, as shown in FIGS. 1 and 8A through 8F, and as described more fully below.

The dimensions of the fixed nests 62 are preferably such that the microplates 22, when inserted into their respective storage locations 28 by the robotic means 30, have their front edges 23 protruding from the respective storage location 28 sufficiently to just clear contacting relation with the inner skin 86*c* of the baffle wall 86. In this manner, the microplates 22 have limited radially outward travel available before contacting the baffle wall 86, and are thereby prevented from accidentally falling out of their respective storage locations 28 upon movement or vibration of the carousel 50 or of the storage module 26, yet are radially indexed with sufficient accuracy for accurate robotic gripping by the robotic means 30, without the need for separate plate locators positioned on the nests adjacent to the radially outer periphery of the carousel 50, as required by, for example, the Hass device illustrated in published U.S. patent application Ser. No. 10/735,866.

It will be appreciated that, in order to provide for the previously mentioned greater design flexibility in relation to the placement of a plurality of robotic means 30 at different positions around the periphery of a particular storage module 26, and for allowing access by each of said robotic means 30 from said different positions to the interior of each storage module 26, and in order to lessen the time necessary for any particular robotic means 30 to access a specific microplate 22 contained within a storage location 28, it is desirable that not only the curved sidewall portion 44 of each such module 26 be rotatable about the central axis "A", but also that the baffle wall 86 also be similarly mounted on the base member 52 so as to be able to bring the second door opening 88 into radial registry (i.e. alignment) with the first door opening 54 and a respective nest 62 containing the specific storage location 28 housing a target microplate 22. As best seen in FIGS. 3A, 3C and 3D, this may be accomplished in a substantially similar manner to the rotational mounting of the sidewall portion 44. That is, a raised circular track 130 is affixed to the bottom wall portion 48 of the housing 42, which track 130 frictionally engages a series of roller wheels 132 arranged around the bottom edge of the baffle wall 86 in downwardly projecting, substantially evenly spaced relation therearound. An external low friction seal 134 and an internal low friction seal 136 are preferably provided adjacent the lower ends of the outer skin 86*a* and the inner skin 86*c* for sliding contact with the sidewalls of the circular track 130 so as to radially locate the baffle wall 86 relative to the track 130 as it rotates and to improve hermetic sealing with the circular track 130. These low friction seals 134 and 136 may be constructed from nylon, graphite impregnated nylon, or any other low friction material. As best seen in FIGS. 3A and 3C, a pair of circular brush seals is preferably attached to the baffle wall 86 adjacent its the top edge, in frictional contact with the top wall portion 46 of the housing 42, thereby to improve hermetic sealing therewith. The pair of brush seals is comprised of an outer seal 138*a* attached to the top of the outer skin 86*a* and an inner seal 138*b* attached to the top of the inner skin 86*c*. In this manner, the curved sidewall portion 44 of the housing 42 is able to rotate in either rotational direction about the axis "A" in order to bring the second door opening 88 into aligned and misaligned radial registry with the first door opening 54 and any selected one of the nests 62 of the carousel 50.

Rotation of the baffle wall 86, as just described, is under the driving force of a fourth electrical motor 118 which is mounted atop the first electrical motor 74. As previously described, the first electrical motor 74 is mounted atop the central support column 60. Both of the fourth 118 and first 74 electrical motors are of congruent circular plan outline and are each centered about the axis "A". The fourth electrical motor 118 has an outer cylindrical second drive collar 140 which engages, for rotation therewith, a cylindrical fourth drive plate 142. The fourth drive plate 142 has arranged about its peripheral edge, in downwardly depending relation therefrom, a fifth magnetic ring member 144. The fifth magnetic ring member 144 extends substantially around the circumference of the fourth drive plate 144. The fifth magnetic ring member 144 may be formed as a permanent magnet (as illustrated), or may be formed as an electromagnet (not illustrated), in which latter case additional circuitry and power supply means to provide for energization of the electromagnet would additionally be required. It is believed that the design and provision of such circuitry and power supply means are within the routine competence of an ordinary person skilled in this art. A sixth magnetic ring member 146 of opposite magnetic polarity to the fifth magnetic ring member 144 is affixed to the top edge of the baffle wall 86 between the outer 86*a* and inner 86*c* skins of the baffle wall 86 in upwardly projecting relation adjacent its circumferential outer edge for rotation therewith upon rotation of the baffle wall 86, as best seen in FIGS. 3A and 3C. The sixth magnetic ring member 146 lies beneath the top wall portion 46 of the housing 42 in underlying alignment with the fifth magnetic ring member 144. With this arrangement, rotation of the fourth electrical motor 118 causes rotation of the fourth drive plate 142 with its attached fifth magnetic ring member 144. Thus, such rotation of the fourth drive plate 142, in turn, exerts a moving magnetic force on the sixth magnetic ring member 146 therebelow, which force drags the sixth magnetic ring member 146 (together with the attached baffle wall 86) in the same rotational direction as the fourth drive plate 142. In this manner, the fifth magnetic ring member 144 and the sixth magnetic ring member 146, mounted respectively on the fourth drive plate 142 and the top edge of the baffle wall 86, combine to form a fourth magnetic coupling means 148 (see FIG. 3C) acting on the baffle wall 86 through the top wall portion 46 of the housing 42, which fourth magnetic coupling means 148 is capable of driving the baffle wall 86 in either rotational direction under the control of the fourth electrical motor 118 for selective radial alignment (or misalignment) at any particular time (as called for by the programmed computer 34, and with the coordinated rotation of the carousel 50) of the second door opening 88 with the first door opening 54. Of course, it is thermally more efficient to misalign the first 54 and second 88 door openings from radial registry with one another to trap heat (or cold) within the housing 42, when it is not necessary to open the door member 92 to retrieve or return a microplate 22.

In order to control the temperature within the housing 42, an environmental control means 149 is also provided on each storage module 26. The environmental control means 149 may have its components constructed and otherwise arranged to cool the interior of the housing 42 (i.e. as a refrigerated internal environment), to warm the interior of the housing (i.e., as an incubated internal environment), or to do both (i.e., as a reversible heat pump), depending upon the needs of an end user. In any of these cases, the components of the environmental control means 149 are substantially the same, although their relative size to one another and exact arrangement may change in a routine manner according to the specific requirements of the end user, as is well known in the refrigeration and heating arts. Accordingly, the environmental control means 149 is depicted in the Figures somewhat diagrammatically, it being appreciated by those skilled in the art that significant variation in the precise location and arrangement of the various components thereof may occur without departing from the spirit or scope of the present invention. In the embodiment described herein in detail, for the sake of simplicity, the environment inside the housing 54 will be a refrigerated environment.

The environmental control means 149 includes what amounts to a small heat pump, and comprises a compressor means 150 and a fan means 152 mounted within the base member 52, and an air flow delivery means positioned within the housing. The air flow delivery means has a first portion comprised of two perforated vertical vent pipes 156 positioned at 180° of rotation from one another on the base member 52 between the sidewall portion 46 and the baffle wall 86 (i.e. in the vestibule 90), and a second portion comprised of the central support column 60, which is also perforated about its periphery. Each of the vertical vent pipes 156 and the central support column 60 is perforated with a series of vent holes 154, which vent holes also comprise part of the air flow delivery means. The fan means 152 is connected by two air supply delivery ducts 160 and one air return delivery duct 162, (which each pass through the bottom wall portion 48 of the housing 42) to the base of the perforated vertical vent pipes 156 and to base of the central support column 60, respectively. For ease of illustration, only one air supply delivery duct 160 is shown in the figures connected to one of the perforated vertical vent pipes 158. It will be understood that a second air supply delivery duct (not shown) similarly connects the fan means 152 to the base of the other perforated vertical vent pipe 156. The fan means 152, the air supply delivery ducts 160 and the air return delivery duct 162 also comprise part of the air flow delivery means. Preferably, the air delivery ducts 160 provide positive air pressure from the fan means 152 to the vertical vent pipes 156 to which they are connected. Such air under positive pressure then exits through the perforations 154 into the vestibule 90 of the housing 42. Return air is drawn from the centre of the housing through fine perforations (not visible) positioned in the inside perimeter wall 69 (as illustrated by arrow "C" in FIG. 3B) and thence through perforations 154 in the central support column 60, traveling downward therein to the return air delivery duct 162, which acts as a return air duct for supplying the fan means 152. In this manner, air within the housing 42 is continuously re-circulated by the fan means 152, and the heat load created by the compressor means 150 and the fan means 152 is removed from the housing 42 into the base member 52. Of course, the system could be ducted to run in reverse: i.e., the duct 162 could be connected to the positive pressure side of the fan means 152 and the duct 160 could be connected to the negative pressure side of the fan means 152. Both arrangements offer acceptable levels of utility.

The environmental control means 149 of the first embodiment further includes an expansion valve 164 which is connected on its outlet side to a supply line 176 that supplies refrigerant gas at, or near, the boiling temperature of the gas, and under low pressure, to a series of evaporator coils 166 which spiral upwardly through the housing 42 around the periphery of each of the central support column 60 and the two perforated vertical vent pipes 158. For simplicity of illustration, a connection by supply line 176 to only the evaporator coils 166 spiralling around the central support column 60 is shown in the Figures. It will be understood that second and third supply lines 176 (not shown) similarly connect the expansion valve 164 to the evaporator coils 166 spiralling around the two perforated vertical vent pipes 158, 158. Such spiraling is arranged to run between the pattern of the perforations 154, such that the air flow to and from said perforations 154 is maximized in the vicinity of the evaporator coils 166. In this manner, heat from the interior of the housing is absorbed from the air of the housing 42 by the relatively cool low pressure gaseous refrigerant in the evaporator coils 166, causing the temperature of this refrigerant gas to rise. The heated refrigerant gas in the evaporator coils 166 returns to the compressor means 150 by way of a suction line 174 running between the two. Again, for simplicity of illustration, only one suction line 174 is shown, whereas, in reality, there would be three of such lines interconnected between the evaporator coils 166 and the compressor 150. The refrigerant gas is compressed by the compressor means 150, causing its temperature to further rise. The hot refrigerant gas is sent from the compressor means 150, by way of a supply line 172, to condenser coils 168. Another fan means (not shown) pulls ambient air (i.e., from outside the housing 42) into the base member 52 through the vent grill 178 and pushes it by appropriate air ducting (not shown) across the condenser coils 168, to exit from the base member 52 through a second vent grill (not shown) on the opposite side of the base member to the vent grill 178. This action draws a significant amount of heat from the hot refrigerant gas in the condenser coils 168, which is sufficient to cause a phase shift from hot gas under high pressure to a hot liquid under high pressure. The hot liquid under high pressure passes from the condenser coils 168 to the expansion valve 164 by means of an expansion valve supply line 170. Transit of the hot liquid under high pressure through the expansion valve 164 significantly reduces the pressure on the hot refrigerant Liquid, creating conditions susceptible to its evaporation. The refrigerant under low pressure and at or near its boiling point, passes on (through the supply line 176) to the evaporator coils 166, where it is able to absorb heat from the air from the housing 42 passing over the evaporator coils 166. This absorption of heat causes a phase shift of the refrigerant from liquid to gas as it passes through the evaporator coils 166 on its way back to the condenser means 150, via the suction line 174. The cycle repeats itself, as called for by a thermostatic means (not shown) under the control of the computer means 34 programmed with the control system software 36.

The robotic means 30 shown in FIG. 1 is positioned exterior to the storage module 26 and adjacent to the base member 52 of the storage module 26. The robotic means 30 may be any commercially available robot having the described degrees of rotational movement, horizontal and vertical travel and dexterity. Typically, such a robotic means 30 would have, as illustrated in FIG. 1, two opposed finger members 188 configured to grip the lateral edges of a microplate 22. The finger members 188 are moveable laterally relative to a hand portion 180, which is, in turn, pivotally attached to a forearm portion 182, which in turn is pivotally attached to an upper arm portion 184, which is in turn pivotally attached to a shoulder arm portion 186. The shoulder arm portion 186 is pivotally mounted on a shoulder plate 190, and the shoulder plate is adapted to move up and down in both vertical directions, as indicated by double-headed arrow "B" in FIG. 1, through a range of motion sufficient to place the hand portion at a vertical level adjacent any one of the microplates 22 in the nests 62. The finger members 188 are adapted to grip any one of the microplates 22 positioned in any one of the storage locations presented in a nest 62, when said nest 62 is simultaneously aligned with the first 54 and second 88 door openings and the door member 92 is in its open configuration, as previously described and as illustrated in FIG. 1. Thereafter, the robotic means 30 retracts its hand portion 180 in a substantially straight path through the second door opening 88 in the baffle wall 86 and through the first door opening 54 in the sidewall portion 44, to withdraw the microplate 22 free of the housing 42. The door member 92 may be closed at this time, or left open for removal or return by the robotic means 30 of a subsequent microplate 22. After removal of a microplate 22, the robotic means 30 is free to swing its hand 180 and arm portions 182, 184, 186 about their respective axis of motion to bring the microplate 22 over the head area 38 of the microplate conveyor 40, whereupon the shoulder plate 190 may be lowered (or raised, as the particular situation requires) to position the gripped microplate 22 upon the microplate conveyor in the head area 38. Once so positioned, the finger members 188 are relaxed by the robotic means 30 to release the microplate 22 onto the microplate conveyor 40 (or other workstation, depending upon the precise configuration of the system 20), for subsequent processing, as previously described. The robotic means 30 is then free to move on to its next programmed task.

The robotic means is in electrical connection with the computer 34, which computer receives inputs from sensors (not shown) conventionally incorporated into the various components of the storage module 26, the robotic means 30 and the balance of the laboratory analysis system 20. In turn, the computer 34, under the influence of the control system software 36, provides sequenced control signals to the various motors of the described components of the robotic means 30, the storage module 26 and the microplate conveyor 40 so as to provide for the required sequence of events. Also, individual machine readable identifying indicia (not shown) is preferably provided on each of the microplates 22, so that its position within the laboratory analysis system 20 can be identified at all times by the control system software 36. Such identifying indicia may take the form of, for example, bar codes, in which case suitable bar code readers (not shown) are conventionally mounted on the movable portions of the robotic means 30 to confirm the unique identity of a particular microplate 22 before gripping (or ungripping) of same by the robotic means 30 as aforesaid. Alternatively, Radio Frequency Identification ("RFID") tags can be used on the nests 62 and/or the microplates 22, and suitable sensors may be conventionally located on the movable portions of the robotic means 30 to confirm the unique identify of the nests 62 and microplates 22 for subsequent interaction therewith by the robotic means 30 and tracking of the movement thereof trough the laboratory analysis system 20 by the control system software 36 running on the computer 34.

While various makes and models of 4 or 5 axis SCARA robotic means can be adapted for use with the present invention, two specific examples suitable for this application are the KiNEDEx™ series of robots, available from Peak Robots, Inc., of Colorado Springs, Colo., USA, and the CRS Vertical Array Loader (VAL)series of robots available from Thermo Electron Corporation of Burlington, Ontario, Canada.

To describe the basic operation of a storage module according to the invention, we will now have particular regard to FIGS. 1 and 2 and to FIGS. 7A through 7D. FIGS. 7A through 7D are a sequence of sectional views, similar to FIG. 3B, showing operative movement of the carousel 50, the curved sidewall portion 44, the door member 92 and the baffle wall 86 of the storage module 26 of FIGS. 1 and 2 to facilitate access from the exterior of the housing 42 to a particular microplate (the target microplate 21'") stored in a particular nest (the "target nest 62'") within the housing 42. We start with a loaded storage module 26 with its door member 92 in the closed configuration, at a 6 o'clock rotational orientation, as depicted in FIG. 2. The storage module may have had its carousel 50 loaded manually, or by use of the robotic means 30 of FIG. 1 retrieving a sequence of microplates 22 from the conveyor means 40 and loading same into the storage locations 28, or indeed by another robotic means (not shown) placed in close proximity to the base member 52 in circumferentially spaced relation from the robotic means 30. In either event, when the control system software 36 calls for a particular microplate 22' to be processed, it causes the computer 34 to send a control signal to the first electrical motor 74 to rotate the carousel 50 (through the agency of the first magnetic coupling means 84 and as indicated by the double headed arrows in FIG. 7A) an appropriate amount to bring the target nest 62' containing the target microplate 22' into operative alignment at the 6 o'clock rotational position with the robotic means 30, as shown in FIG. 7A. A second control signal is then sent by the computer 34 to the second electrical motor 102 to rotate the sidewall portion 144 of the housing 42 (through the agency of the second magnetic coupling means 116) an appropriate amount to bring the first door opening 54 into radially operative alignment with the target nest 62' and target microplate 22' as shown in FIG. 7B. Thereafter, a third control signal is then sent by the computer 34 to the third electrical motor 104 to rotate the door member 92 in the direction of the arrow of FIG. 7C (through the agency of the third magnetic coupling means 128)from its closed configuration (as shown in FIGS. 2 and 7B) to its open configuration (as shown in FIG. 7C). A fourth control signal is then sent by the computer 34 to the fourth electrical motor 118 to rotate the baffle wall 186 (through the agency of the fourth magnetic coupling means 148) an appropriate amount to bring the second door opening 88 into radially operative alignment with the target nest 62' and the first door opening 54 (as seen in FIGS. 1 and 7D). The order of the control signals is not essential; it is only essential that the end result be the same: i.e., that the target nest 62', the second door opening 88, and the first door opening 54 be radially aligned to permit the robotic means 30 to thereafter reach into the interior of the housing 42 to retrieve the target microplate 22 by gripping thereof about its lateral edges by clamping action of the finger members 180 and retraction of the hand portion 180 and arm members 182, 184, and 186 to pull the microplate 22 clear of the storage housing 42 as previously described. The robotic means 30 is then instructed by the computer 34 to rotate the arm members 182, 184 and 186 about their respective axis's to bring the hand portion 180 over the head area 38 of the conveyor means 40. A further control signal instructs the robotic means 30 to lower the shoulder plate 190 so as to position place the hand portion 180 and the microplate 22 on the head area 38 of the conveyor means 40 for release thereat by the finger members 180. The conveyor means 40, under control by the computer 34, carries the microplate 22 away for subsequent processing by the laboratory analysis system 20 the arm members 182, 184 and 186 may then be retracted and moved vertically to retrieve a further microplate 22, or may be rotated to another adjacent workstation (not shown), or to another adjacent storage module (as discussed below) to grippingly engaged a different microplate 22 and return it to a storage location 28 in the target nest 62', or to another nest of the carousel 50 (after appropriate rotation of the carousel 50). The door member 92 is closed by an appropriate control signal sent to the third electrical motor 104 when access to the interior of the housing 42 is no longer required by the control system software 36.

FIGS. 8A through 8F are a sequence of sectional views (on a plane similar to that of FIG. 3B) of three storage modules 30 of the same type as already described with reference to FIGS. 1 through 7D, inclusive, positioned in proximity to one another to form a cluster of three storage modules 30, with a single robotic device 30 positioned in close proximity to each of the three modules 30. A microplate conveyor (not shown) similar to that shown in FIGS. 1 and 9 has been omitted for ease of illustration from FIGS. 8A through 8F, but is advantageously positioned in a central location to the bottom center of each of FIGS. 8A through 8F, with its head area 38 in operative range of the hand portion 180 and arms 182, 184 and 186 of the robotic means 30, so as to provide for the transfer of a target microplate 22' from the nests of any one of the three storage modules 26 depicted in FIGS. 8A through 8F to said head area 38 for subsequent processing by other components of the laboratory analysis system 20.

From FIGS. 8A through 8F, the reader will appreciate the modular nature of storage modules 26 constructed according to the present invention, how microplates can be passed from one storage module to another, and the flexibility of design options available for combining these modules 26 with one another, with one or more robotic means 30, and with other prior art workstations (not shown) to form a complex automated laboratory analysis system.

Figure 8A:
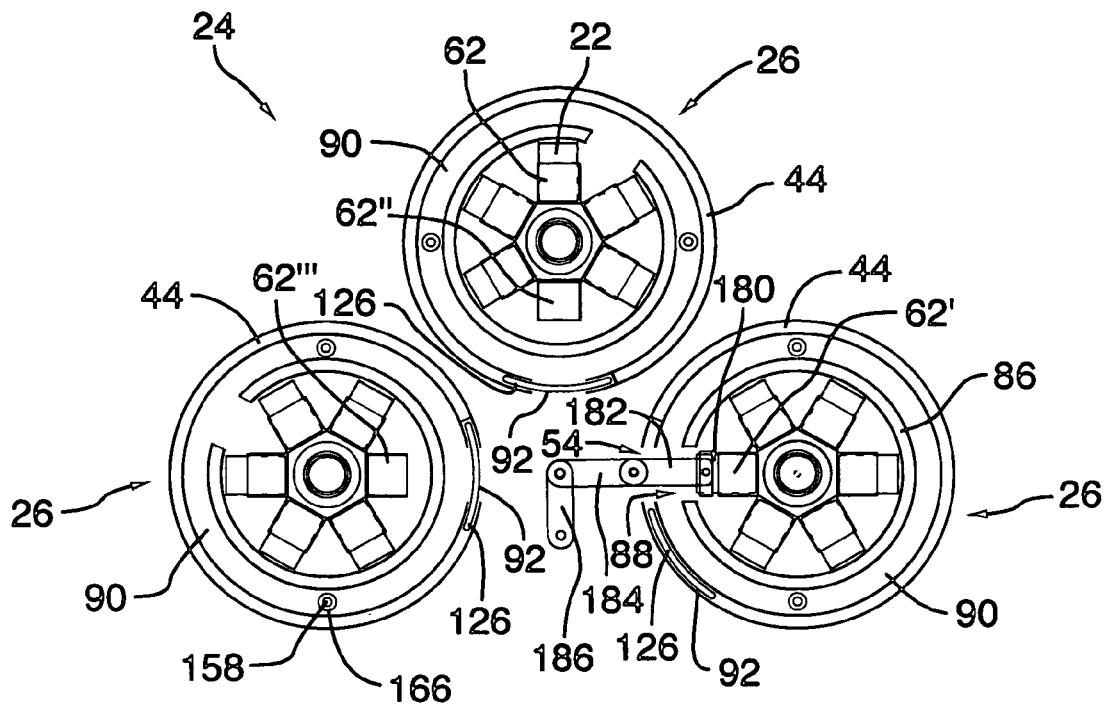
FIGS. 8A through 8F are a sequence of top plan views (on a similar plane to that of FIG. 3B) of an alternate embodiment of a storage system according to the invention having a plurality of storage modules positioned in proximity to one another to form a cluster of said storage modules, with a robotic device positioned in close proximity to each of said modules; and, FIG. 9 is a view similar to FIGS. 8A through 8F, illustrating a further alternate embodiment of a storage system according to the invention having a plurality of peripheral storage modules arranged in a cluster around a central storage module, with a robotic devices interposed between each one of said peripheral storage modules and said central storage module.
Figure 8B:
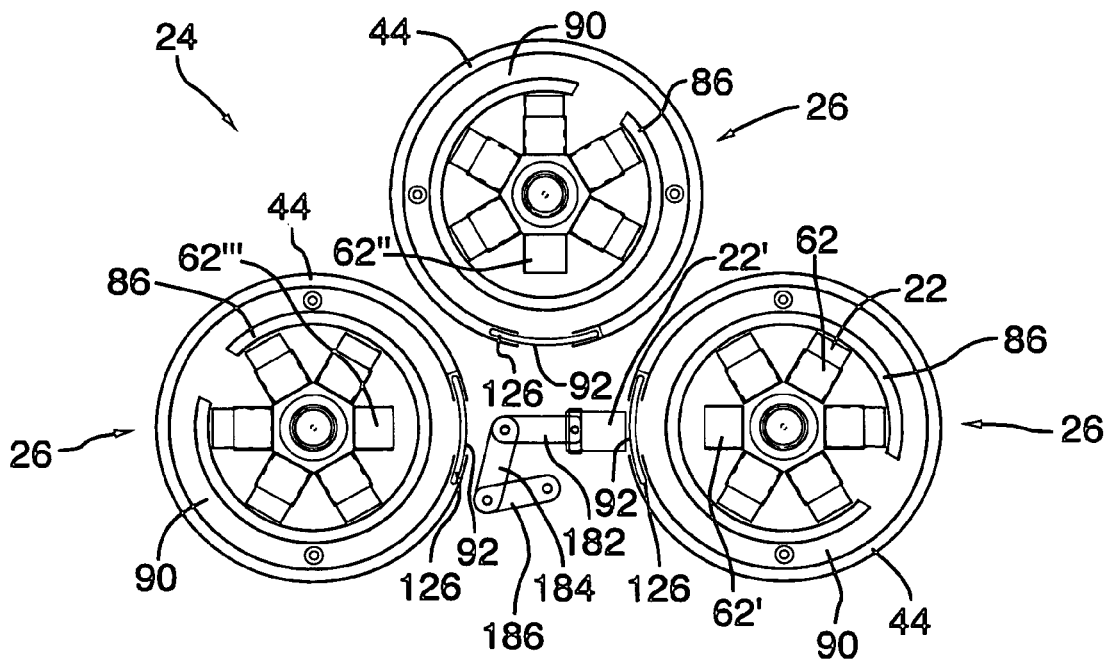
Figure 8C:
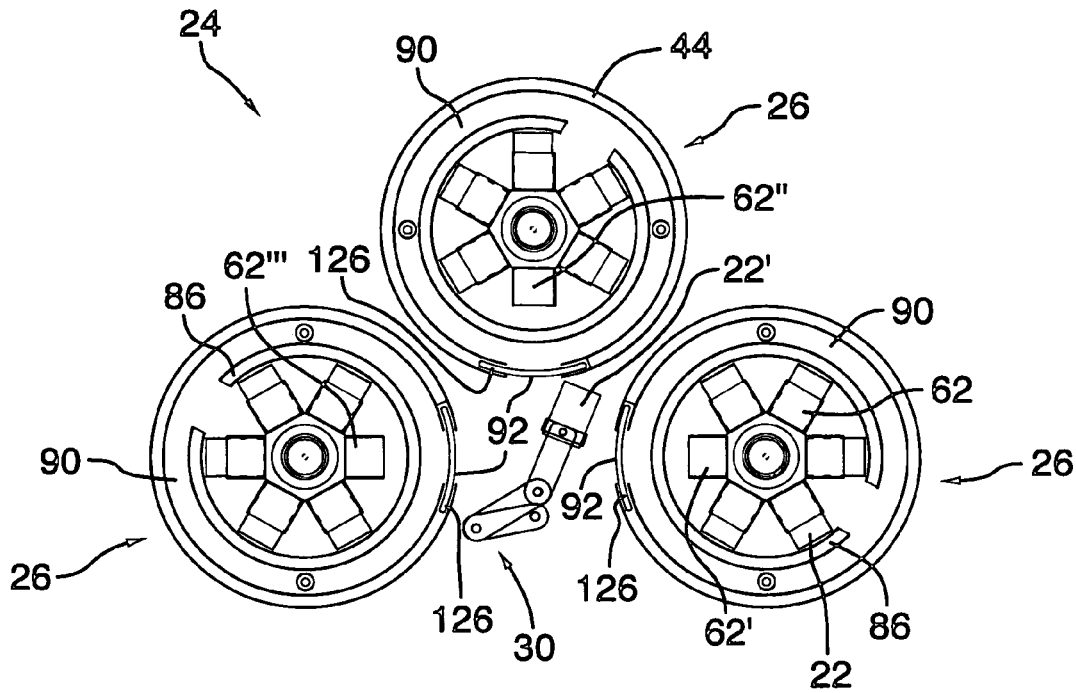
Figure 8D:
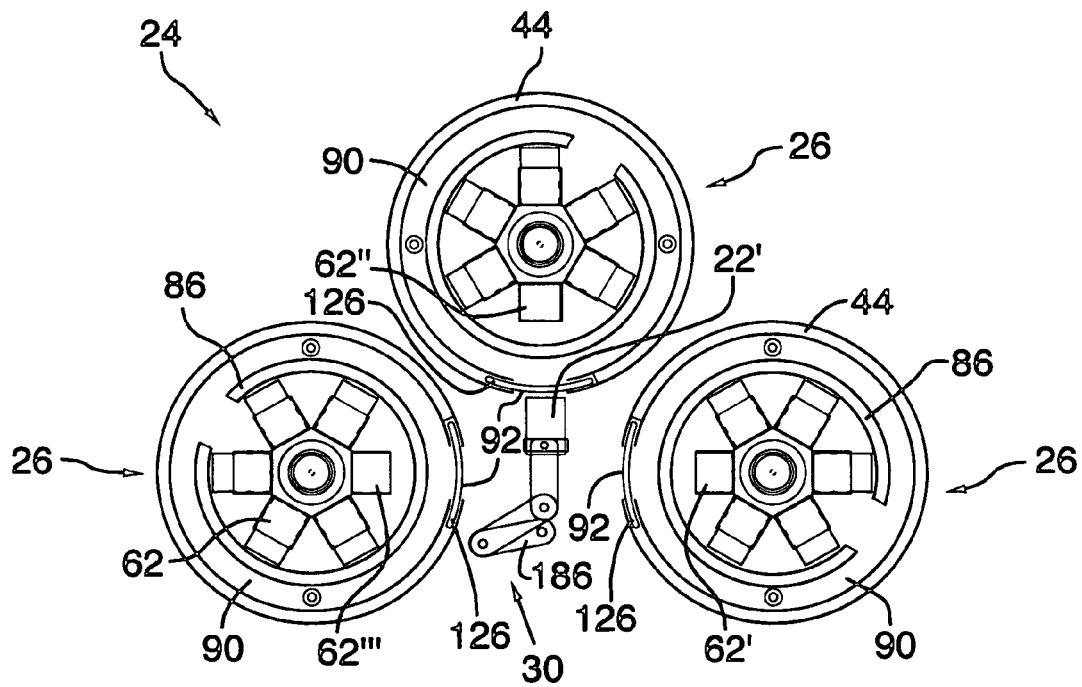
Figure 8E:
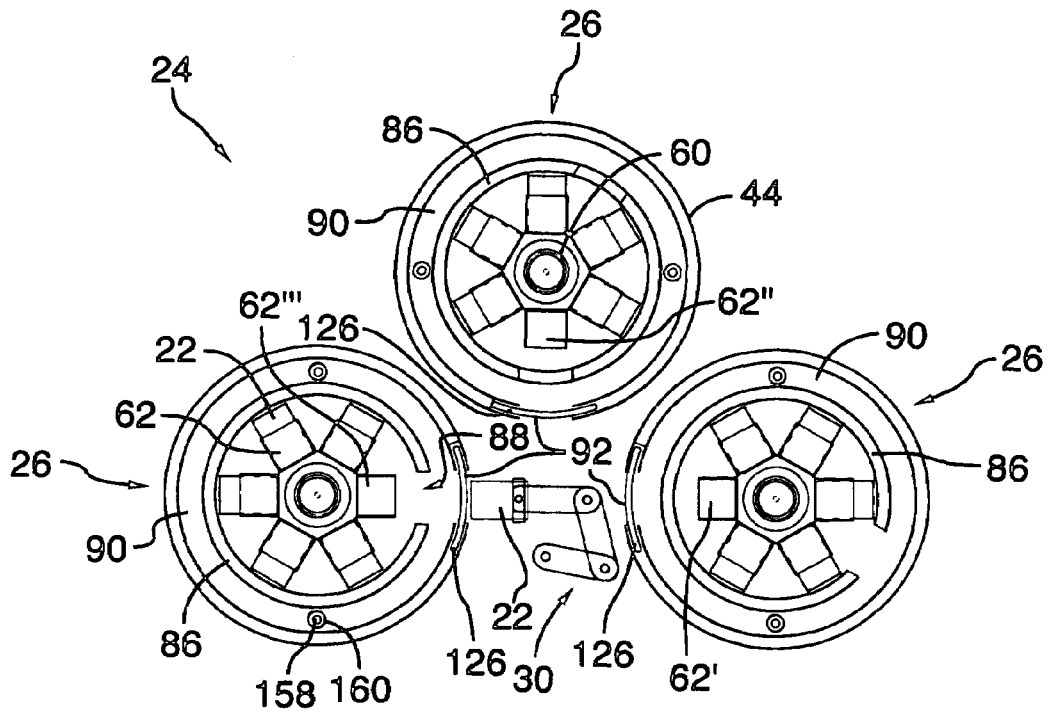
Figure 8F:
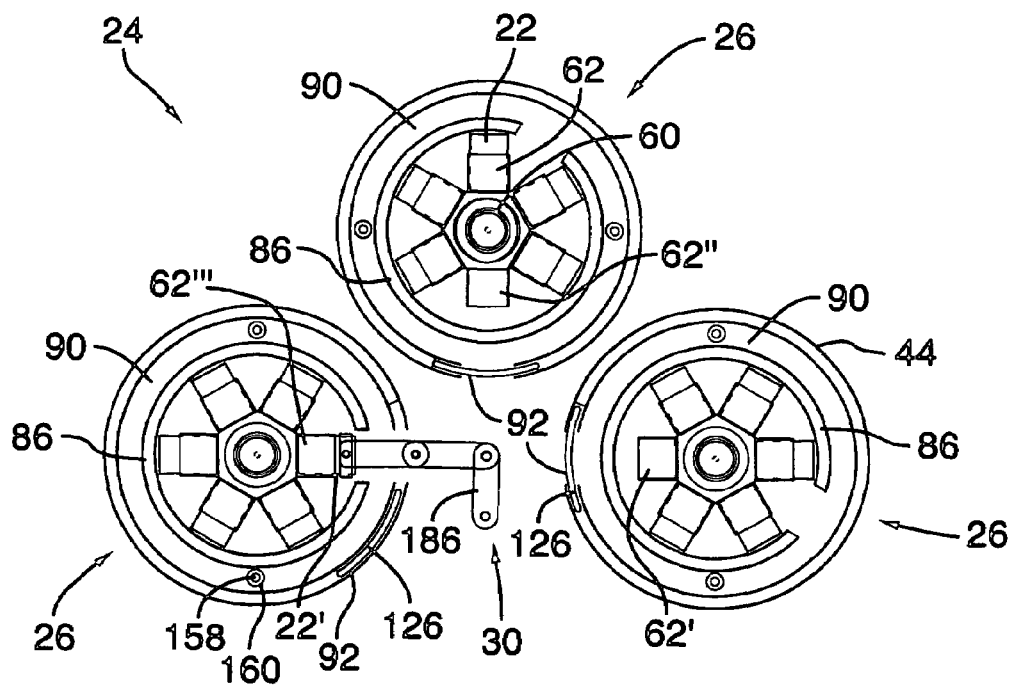

In FIG. 8A it will be seen that three storage modules 26 have been grouped together in proximity to one another, with the center point of such modules 26 located one each at the apices of a notional equilateral triangle. A robotic means 30 (as described above) is situated within the equilateral triangle, exterior to the housings 42, and is in adjacent relation to the base members 52 of all three of the storage modules 26. (Parts of the robotic means 30 have been omitted from FIGS. 8A through 8F for ease of illustration.) In FIG. 8A, the hand portion 180 of the robotic means 30 has moved, under control of the computer 34 and control system software 36, into the interior of the right-most storage module 26 through the first 54 and second 88 door openings to grip a target microplate 26' located in a target nest 62'. Thereafter, as depicted in FIG. 8B, the arms 182, 184 and 186 pivot about their respective axis's, as shown, to remove the target microplate 22' from the right-most storage module 26. In FIG. 8C, the arms 182, 184 and 186 have pivoted further, so as to move the target microplate 22' midway between the right-most storage module 26 and the top-most storage module 26. Moreover, in FIG. 8C, the door member 92 of the right-most storage module 26 has been closed, and the sidewall 44 and baffle wall 86 have been rotated out of radial alignment (to minimize thermal leakage), all in response to appropriate signals sent from the computer 34. In FIG. 8D, the arms 182, 184 and 186 have pivoted further still, so as to move the target microplate 22' into radial alignment with an empty nest 62" located in the top-most storage module 26. If the control system software 36 called for storage of the target microplate 22' in a storage location of the empty nest 62", it could cause the sidewall 44 and baffle wall 86 of the top-most storage module 26 to radially align therewith and the door member 92 to slide open to permit entry of the hand portion 180 for this purpose. However, in the illustrated sequence, this is not the case. Therefore, the robotic means 30 continues to move the target microplate 22' past the top-most storage module 30 to the configuration shown in FIG. 8E, where the arms 182, 184 and 186 have pivoted further, as shown, so as to move the target microplate 22' into radial alignment with an empty nest 62'" located in the left-most storage module 26. Moreover, in FIG. 8E, the door member 92 of the left-most storage module 26 has been moved to its open configuration, and the sidewall 44 and baffle wall 86 of the left-most storage module 26 have been rotated into radial alignment with the empty nest 62'" in response to appropriate signals sent from the computer 34. The left-most storage module 26 has in this manner been prepared to receive insertion of the target microplate 22', which insertion into a selected storage location in the empty nest 62'" is completed by extension of the arms 182, 184 and 186, as shown in FIG. 8F. Thereafter, the arms 182, 184 and 186 and the hand portion 180 of the robotic means 30 are retracted from the interior of the left-most storage module 26 and the door member 92 of the left most storage module 26 is moved, under control of the compute 24, to its closed configuration. In this manner, the target microplate 22' has been transferred from the storage locations 28 of a selected storage module (being the right-most storage module 26 of FIGS. 8A to 8F) to one or more locations (being the storage locations 28 in the target net 62'" of the left-most storage module 26, or the head area 38 or other workstation (not shown)) exterior to the housing 42 of said right-most storage module 26. The robotic means 30 is then free to move on to its next task.

Figure 9:
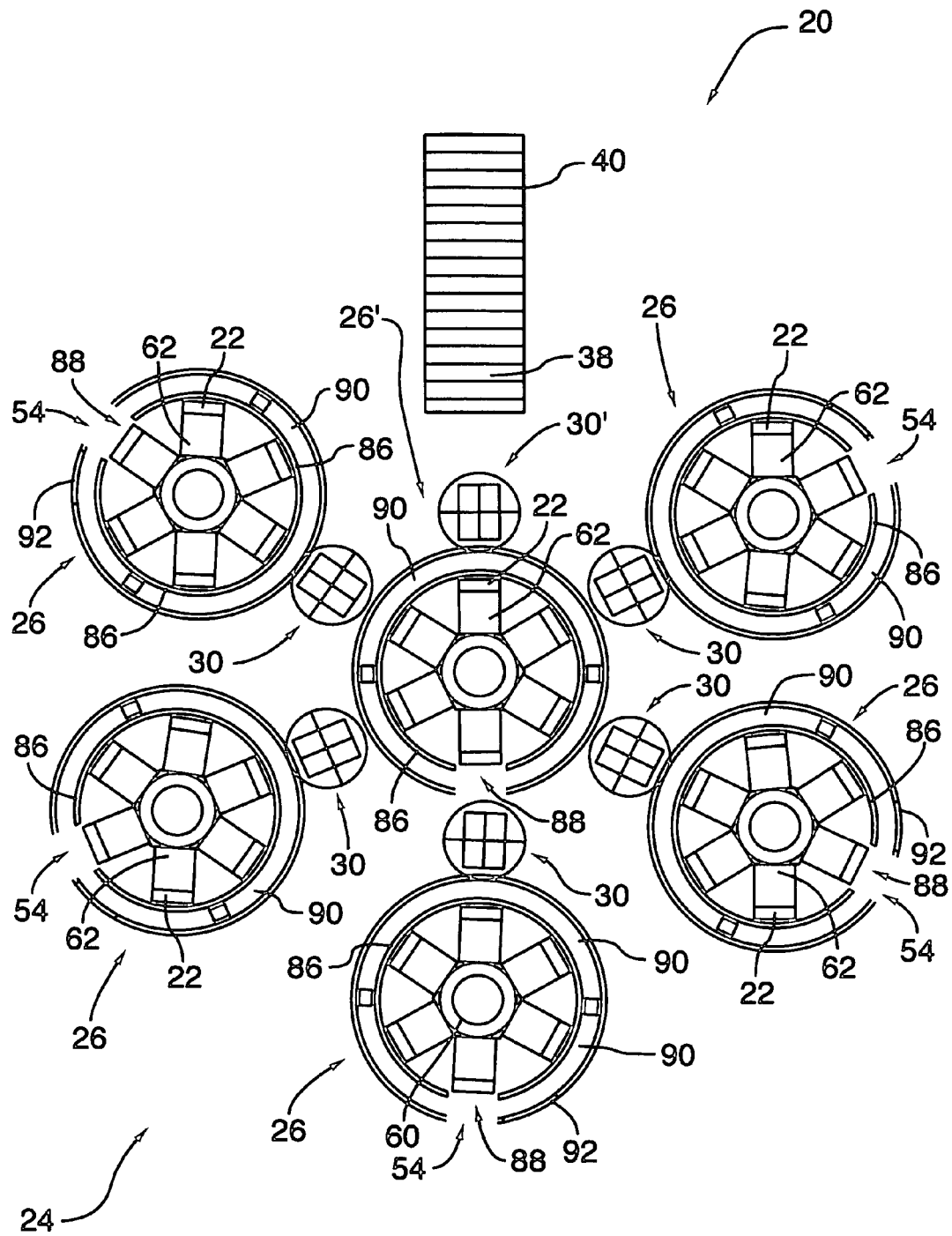

FIG. 9 is a top sectional view similar to FIG. 8A, illustrating an alternate exemplary layout for a laboratory analysis system wherein five peripheral storage modules 26 (constructed as previously described) are arranged in proximity to one another around a central storage module 26' (constructed as previously described) to form a cluster of six storage modules 26,26'. The storage modules 26 and 26' illustrated in FIG. 9 have been grouped together in proximity to each other and to the central storage module 26', such that the center point of each of the five peripheral storage modules 26 is located one each at the apices of a notional pentagon. The central storage module 26' is located within the pentagon. Five robotic means 30' are positioned one each in operatively close proximity to the base member 52 of each of the peripheral storage modules 26 and to the base member of the central storage module 26'. In this manner, each one of the robotic means 30' is positioned within operatively close relation to at least two of the storage modules 26 and 26' of the cluster. By the term "operatively close proximity" it is meant, in this specification and the claims appended hereto, that the robotic means 30' being referenced is sufficiently close to each of the adjacent two storage modules 26 and 26' that it is capable of having its robotic hand and fingers reach into one of the storage modules 26 or 26' in the same general manner hereinbefore described, to grip and remove a microplate 22 selected by the computer means 34 from a respective storage location (nest) in said one of the storage modules 26 or 26', and to thereafter transfer said selected microplate 22 to the other one of the two storage modules 26 or 26' in the same general manner as already described in relation to FIGS. 8A through 8F, or vice versa. It will be appreciated that with the arrangement shown, and with analogous arrangements, any one of the microplates 22 in any one of the storage modules 26 or 26' can be transferred to any other one of the storage modules 26 or 26' under the control of the computer means 34 programmed with appropriate control system software 36, although more than one of such transfers may be necessary to effect the desired transfer, depending upon the starting position of the selected microplate 22 and its desired end position.

There is also present in the laboratory analysis system 20 of FIG. 9 a microplate conveyor 40 similar to that shown in FIG. 1 and having a head area 38. A sixth robotic means 30 is shown interposed between the central storage module 26' and the microplate conveyor 40. This robotic means 30' is substantially the same as the other robotic means 30 illustrated in FIG. 9, and is adapted and otherwise positioned to reach into the housing 42 of the central storage module 26' to remove selected microplates 22 in seriatim from the nests 62 therewithin, in the same general manner as described above, for placement on the head area 38 for subsequent transport to other workstations (not shown) of the laboratory analysis system 20, or to return said microplates 22 to selected nests 62 of the central storage module 26', all under control of the computer means 34, as called for by the control system software 36. It will be appreciated that the array of peripheral storage modules 26 depicted in the cluster of FIG. 9 may be extended outwardly in a regular array away from the central storage module 30' by arranging one or more additional storage modules (not shown) around each of the peripheral storage modules 30 shown, with an additional robotic means 30 positioned in operative proximity to adjacent pairs of such additional storage modules. In this manner, each peripheral storage module 30, may, in effect, become a central storage module to the peripheral storage modules around it, to and from which microplates 22 from all other storage modules in the array may be transferred and pass through. Thus, when all of the robotic means 30, 30' and the storage modules 26 and 26' are electrically connected to the computer 34, the cluster, as a whole becomes a growable modular on-line storage system of indefinite capacity, thereby substantially eliminating the need for a standalone off-line mass storage facility, as required in the prior art.

Other modifications, additions and alterations may be used in the design and manufacture of other embodiments according to the present invention without departing from the spirit and scope of the invention, which is limited only by the accompanying claims. For example, the electrical motors utilized in the storage units 26, 26' need not be direct drive motors as illustrated, but could be of less costly designs utilizing, for example, rack and pinion, or belt drive, mechanisms (not shown). Moreover, the use of more than one door opening in each of the sidewall 44 and baffle wall 86 may be desirous in certain situations (e.g. where access times are critical and interior temperature stability is not). The use of double door members (i.e., a split door member with two halves sliding in opposite circumferential directions to expose one or more of the nests of the carousel) in place of the single door illustrated is also an obvious variant considered by the applicant as clearly within the scope of the present invention as claimed. Also, the wheels 56 mounted on the base member 52 of the storage modules 26 may be power driven by a further motor drive means (not shown) contained within the base member 52, thereby to assist in movement of the storage modules 26, 26' from place to place. Also, while hard-wired electrical connections between the various hardware components of the laboratory analysis systems illustrated are shown and described above, such connections may be hard wired or wireless, not limited to Bluetooth™, 802.11a/b/g and Ethernet type connections. It is also possible to provide a manual override control means (not shown) on each of the storage modules 26, 26' to allow a user to manually access microplates 22, 22' stored in the nests 62, 62' on the carousel 50 mounted within the interior of the respective storage module 26, 26'. Such manual override control could take the form of a liquid crystal display touch screen user interface, operable by a user to set or adjust the environmental settings of the storage module 26, 26' and to rotate the carousel 50, the baffle wall 86 and the sidewall portion 44 in the general manner previously described to align a particular nest 62, 62' on the carousel 50 with the first 54 and second 88 door openings to open the door member 92, so as to allow the user to manually remove (or load) particular microplates 22, 22' in said nests 62,62'.

The invention claimed is:

1. A storage system having one or more storage modules each comprising:
    a substantially cylindrical housing having a curved sidewall portion extending between a top wall portion and a bottom wall portion, said housing being disposed about a central axis;
    a carousel mounted within said housing for rotation about said central axis and having a plurality of storage locations disposed in vertical arrays about said axis to receive articles;
    one or more door openings formed in said sidewall portion to provide for access from the exterior of the housing to at least one of said vertical arrays adjacent to said one or more door openings;
    environmental control means for controlling the temperature within said housing;
    wherein said one or more door openings comprise a first door opening;
    wherein said first door opening is selectively occluded by a door member mounted on the housing and movable between an open and a closed configuration;
    wherein the first door opening axially extends between the top and the bottom wall portions of the housing, and the first door member has a curvature complimentary to the curvature of the sidewall portion;
    wherein the door member moves between said open and said closed configurations by sliding in circumferential nesting relation relative to said sidewall portion of said storage module;
    wherein the environmental control means comprises an air flow delivery means positioned within the housing;
    wherein the housing is mounted atop a base member, and wherein the environmental control means comprises a compressor means and a fan means mounted within said base member.

2. A storage system according to claim 1, wherein rotation of the carousel within the housing is driven by a first electrical motor mounted on the storage module for selective radial alignment of said at least one of said vertical arrays with the first door opening.

3. A storage system according to claim 2, wherein said first electrical motor is drivingly connected to said carousel by a first magnetic coupling means acting on said carousel through at least one of said top wall and said bottom wall portions of the housing.

4. A storage system according to claim 3, wherein said sidewall portion is mounted so as to be rotatable about the central axis to align said first door opening with a selected one of said vertical arrays.

5. A storage system according to claim 4, wherein said rotation of the sidewall portion is driven by a second electrical motor mounted on the storage module.

6. A storage system according to claim 5, wherein said second electrical motor is drivingly connected to said sidewall portion by a second magnetic coupling means acting on said sidewall portion through at least one of said top wall and said bottom wall portions of the housing.

7. A storage system according to claim 6, wherein said movement of the door member is driven by a third electrical motor mounted on the storage module.

8. A storage system according to claim 7, wherein said third electrical motor is drivingly connected to said door member by a third magnetic coupling means acting on said door member through at least one of said top wall and said bottom portions of the housing.

9. A storage system according to claim 8, wherein a substantially cylindrical baffle wall disposed about the central axis and extending between the top wall portion and the bottom wall portion is mounted within the housing between the sidewall portion and the carousel to form a vestibule between the sidewall portion and the baffle wall, said baffle wall having one or more door openings formed therein for alignment with said first door opening to facilitate said access from the exterior of the housing to at least one of said vertical arrays.

10. A storage system according to claim 9, wherein said one or more door openings comprise a second door opening.

11. A storage system according to claim 10, wherein said second door opening axially extends between the top and bottom wall portions of the housing.

12. A storage system according to claim 11, wherein said baffle wall is mounted so as to be rotatable about the central axis to selectively align and misalign said second door opening with said first door opening.

13. A storage system according to claim 12, wherein said rotation of the baffle wall is driven by a fourth electrical motor mounted on the storage module.

14. A storage system according to claim 13, wherein said fourth electrical motor is drivingly connected to said baffle wall by a fourth magnetic coupling means acting on said baffle wall through at least one of said top and bottom wall portions of the housing.

15. A storage system according to claim 14, wherein a first portion of the air flow delivery means is positioned in the vestibule and a second portion of said air flow delivery means is centrally positioned in the housing.

16. A storage system according to claim 15, wherein wheels are mounted on the base member to facilitate selective movement of the storage module from place to place.

17. A storage system according to claim 16, additionally comprising one or more robotic means positioned exterior to the housing and adjacent to the base member of a selected one of said one or more storage modules, said robotic means being constructed and otherwise adapted to reach into the housing of said selected storage module through said first door opening, when said door member is in said open configuration, and through said second door opening, when same is aligned with said first door opening to access the storage locations disposed in said at least one of said vertical arrays to grip and transfer said articles between said storage locations and one or more locations exterior to the housing of said selected storage module.

18. A storage system according to claim 17, having a plurality of said storage modules positioned in proximity to one another to form a cluster of storage modules, with one or more of said robotic means each positioned within operatively close proximity to at least two of the storage modules of said cluster to transfer said articles from the storage locations of any one of the storage modules of the cluster to the storage locations of any other one of the storage modules of the cluster.

19. A storage system according to claim 18, wherein the first, second, third and fourth electrical motors of each of said storage modules of the cluster and each of said one or more robotic means are in electronic communication with a CPU means programmed with control system software so as to bring each of said robotic means and each of said storage modules under the coordinated control of said CPU means so as to form a modular on-line storage system of indefinite capacity.

20. A storage system according to claim 19 wherein the cluster of storage modules is comprised of a centrally positioned storage module, and a plurality of storage modules peripherally arranged around said centrally positioned storage module, and wherein the one or more robotic means is a plurality of robotic means, with at least one of said plurality of robotic means being interposed between each one of said peripheral storage modules and said centrally positioned storage module.

21. A storage system according to claim 18, wherein wheels are mounted on the base member of each of said one or more storage modules to facilitate their selective movement from place to place.

* * * * *